(12) United States Patent
Hiratake et al.

(10) Patent No.: US 8,129,557 B2
(45) Date of Patent: Mar. 6, 2012

(54) PHOSPHONIC ACID DIESTER DERIVATIVE AND METHOD FOR PRODUCING THEREOF

(75) Inventors: Jun Hiratake, Kyoto (JP); Kanzo Sakata, Kyoto (JP); Liyou Han, Kyoto (JP)

(73) Assignee: Kazuhiro Nagai, Uji-shi, Kyoto (JP)

( * ) Notice: Subject to any disclaimer, the term of this patent is extended or adjusted under 35 U.S.C. 154(b) by 772 days.

(21) Appl. No.: 12/096,321

(22) PCT Filed: Nov. 30, 2006

(86) PCT No.: PCT/JP2006/324412
§ 371 (c)(1),
(2), (4) Date: Aug. 26, 2008

(87) PCT Pub. No.: WO2007/066705
PCT Pub. Date: Jun. 14, 2007

(65) Prior Publication Data
US 2009/0163725 A1   Jun. 25, 2009

(30) Foreign Application Priority Data

Dec. 7, 2005 (JP) .................. 2005-354121
Jul. 7, 2006 (JP) .................. 2006-188282

(51) Int. Cl.
*C07F 9/32* (2006.01)
*C07F 9/38* (2006.01)
(52) U.S. Cl. .................. 558/169; 558/70; 560/129

(58) Field of Classification Search .................. 558/169, 558/70; 560/129
See application file for complete search history.

(56) References Cited

FOREIGN PATENT DOCUMENTS

JP   63-027467   2/1988

OTHER PUBLICATIONS

C. Lherbet, et al., Probing the stereochemistry of the active site of gamma-glutamyl transpeptidase using sulfur derivatives of L-glutamic acid, Org. Biomol. Chem., 2004, 2, pp. 238-245.
E. Stole, et al., Interaction of g-Glutamyl Transpeptidase with Acivicin, Journal of Biological Chemistry, vol. 269, No. 34, Aug. 26, 1994, pp. 21435-21439.
R. Stein, et al., Slow-Binding Inhibition of g-Glutamyl Transpeptidase by g-boroGlu, Biochemistry, 2001, 40, pp. 5804-5811.

*Primary Examiner* — Charanjit Aulakh
(74) *Attorney, Agent, or Firm* — Westerman, Hattori, Daniels & Adrian, LLP

(57) ABSTRACT

A phosphonic acid diester derivative represented by the following general formula (1):

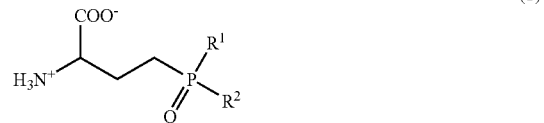

(1)

wherein at least one of $R^1$ and $R^2$ denotes a leaving group.

17 Claims, 2 Drawing Sheets

PHOSPHONIC ACID DIESTER DERIVATIVE AND METHOD FOR PRODUCING THEREOF

CROSS-REFERENCE TO PRIOR APPLICATIONS

This is a U.S. national phase application under 35 U.S.C. §371 of International Patent Application No. PCT/JP2006/324412, filed Nov. 30, 2006, and claims the benefit of Japanese Application No. 2005-354121, filed Dec. 7, 2005, and Japanese Application No. 2006-188282, filed Jul. 7, 2006, all of which are incorporated by reference herein. The International Application was published in Japanese on Jun. 14, 2007 as International Publication No. WO 2007/066705 A1 under PCT Article 21(2).

TECHNICAL FIELD

The present invention relates to a phosphonic acid diester derivative and a method for producing thereof. More specifically, the present invention relates to a phosphonic acid diester derivative which is used for GGT (γ-glutamyl-transpeptidase) inhibitor, and a production method thereof.

PRIOR ART

The phosphonic acid diester derivative of the present invention is a novel compound that has not been reported yet.

Further, acivicin (THE JOURNAL OF BIOLOGICAL CHEMISTRY: 1994 by The American Society for Biochemistry and Molecular Biology, Inc. vol. 269, No. 34, p 21435-21439, Aug. 26, 1994) has been generally used as a GGT inhibitor. The acivicin has been known to act not only on GGT but also on other intravital enzymes.

As another GGT inhibitor is known γ-borono-glutamic acid (Biochemistry, vol. 40, p 5804-5811 (2001)). However, since γ-borono-glutamic acid is a reversible inhibitor, it is difficult to practical use γ-borono-glutamic acid as a GGT inhibitor.

SUMMARY OF THE INVENTION

Therefore, the main object of the invention is to provide a novel phosphonic acid diester derivative and a production method thereof.

Another object of the invention is to provide a phosphonic acid diester derivative having a selective activity on GGT among intravital enzymes and an inhibitory activity for irreversibly inactivating GGT, and a production method thereof.

The invention of claim 1 is a phosphonic acid diester derivative represented by the following general formula (1):

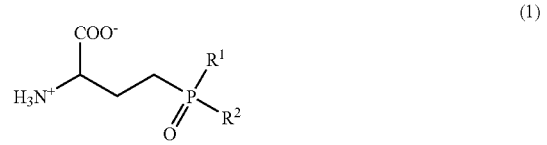

(1)

(wherein at least one of $R^1$ and $R^2$ denotes a leaving group).

The invention of claim 19 is a 2-substituted amino-4-phosphonobutanoic acid metal salt represented by the following general formula (19):

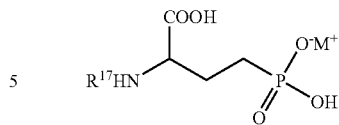

(19)

(wherein M denotes an alkali metal and $R^{17}$ denotes an alkoxycarbonyl group containing an aromatic hydrocarbon group that may have substituent groups).

The invention of claim 20 is a 2-substituted amino-4-phosphonobutanoic acid ester represented by the following general formula (20):

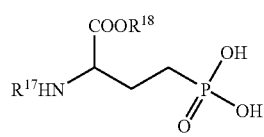

(20)

(wherein $R^{18}$ denotes an aromatic hydrocarbon group that may have substituent groups and $R^{17}$ is defined as described above).

The invention of claim 21 is a method for producing a phosphonic acid diester derivative represented by the general formula (1) described in claim 1 from 2-amino-4-phosphonobutanoic acid, wherein the 2-substituted amino-4-phosphonobutanoic acid metal salt represented by the general formula (19) described in claim 19 is isolated as crystals.

The invention of claim 22 is a method for producing a phosphonic acid diester derivative represented by the general formula (1) described in claim 1 from 2-amino-4-phosphonobutanoic acid, wherein the 2-substituted amino-4-phosphonobutanoic acid ester represented by the general formula (20) described in claim 20 is isolated as crystals.

According to the invention, the phosphonic acid diester derivative represented by the general formula (1) can selectively inactivate GGT among intravital enzymes and irreversibly inactivate GGT.

The above described objects and other objects, features, aspects and advantages of the present invention will become more apparent from the following detailed description of the present invention when taken in conjunction with the accompanying drawings.

BEST MODE FOR PRACTICING THE INVENTION

Figure 1:
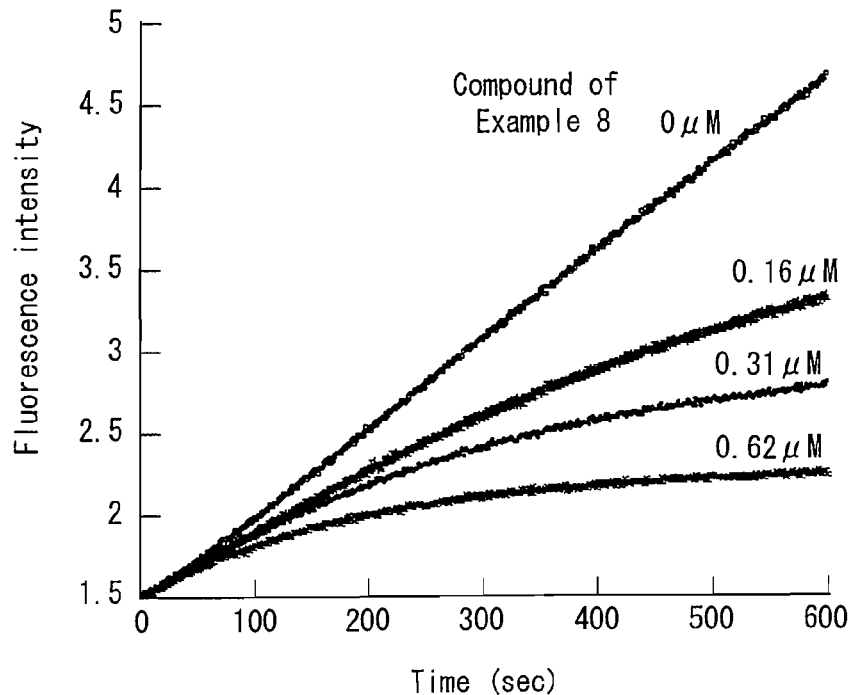
FIG. 1 is a graph showing fluorescence intensity of AMC in relation to the concentration of the compound of Example 8 and the reaction time in the case of causing reaction of the compound and *E-coli* GGT.

The phosphonic acid diester derivative (1) of the invention will be described.

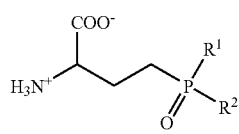
(1)

At least one of $R^1$ and $R^2$ is a leaving group. As the leaving group, those having a dissociation constant $pK_a$ of about 12 or lower are employed. Examples of the leaving group are those represented by the following general formulas (2) to (6).

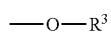 (2)

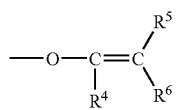 (3)

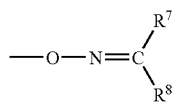 (4)

 (5)

 (6)

$R^3$ denotes an aryl group that may have substituent groups or a heterocyclic group that may have substituent groups and the like, and the aryl group may be a phenyl group and the like. $R^4$, $R^5$, $R^6$, $R^7$, $R^8$, and $R^9$ independently denote a hydrogen atom, an alkyl group that may have substituent groups, an aryl group that may have substituent groups, or an electron-withdrawing group and they may be same or different one another. Examples of the electron-withdrawing group are a halogen atom, a carbamoyl group, a carbonyl group, a cyano group, an alkylsulfanyl group, an arylsulfanyl group, a carboxy group, and the like. Among substituent groups of $R^4$-$R^8$, neighboring two substituent groups may be bonded to form a ring.

In the phosphonic acid diester derivative (1), the following phosphonic acid diester derivative (21) wherein $R^1$ is $OR^{10}$ and $R^2$ is $OR^{11}$ is preferable.

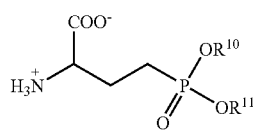
(21)

In the phosphonic acid diester derivative (21), $R^{10}$ and $R^{11}$ denote groups other than a hydrogen atom and at least one of $OR^{10}$ and $OR^{11}$ is a leaving group. Examples of the leaving group may be substituent groups represented by the general formulas (2) to (4) and particularly —O—$R^3$ of the general formula (2) is preferable and especially $R^3$ is preferably an aryl group that may have substituent groups. In this case, it is preferable that $R^{10}$ denotes an alkyl group that may have substituent groups or an aryl group that may have substituent groups and $R^{11}$ denotes an aryl group that may have substituent groups. Further, at least one of $OR^{10}$ and $OR^{11}$ is preferable to have the same GGT substrate structure or similar to that structure. Particularly, in the case of human GGT, preferable is a structure containing a carboxy group or its equivalent group bonded to the terminal carbon atom and having 6 to 8 atoms, excluding hydrogen atoms, away from the oxygen atom bonded to phosphorus atom to the terminal.

Next, the alkyl group that may have substituent groups in $R^{10}$ will be described.

Substituent groups of the alkyl group that may have substituent groups may include a phenyl group that may have substituent groups, a nitrogen-containing heterocyclic group, an alkylsulfanyl group, an arylsulfanyl group, a hydroxy group, a carbamoyl group, an amino group, a guanidino group, an alkoxy group, an amido group, a carboxy group, an equivalent group of a carboxy group, and the like.

An alkyl chain of the alkyl group that may have substituent groups may be a straight chain or a branched chain. Especially the following is preferable.

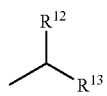
(7)

$R^{12}$ denotes an alkyl group that may have substituent groups, an aryl group that may have substituent groups, a hydrogen atom or the like.

Substituent groups of the alkyl group that may have substituent groups of $R^{12}$ include a phenyl group that may have substituent groups, a nitrogen-containing heterocyclic group, an alkylsulfanyl group, an arylsulfanyl group, a hydroxy group, a carboxy group, a carbamoyl group, an amino group, a guanidino group, an alkoxy group, and an amido group.

An alkyl group that is substituted with the phenyl group that may have substituent groups is preferably the following.

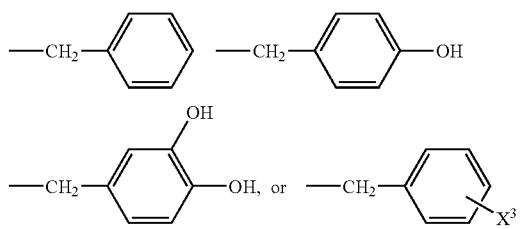

$X^3$ denotes an alkoxy group, a lower alkyl group or the like and examples of the lower alkyl group include such as linear or branched alkyl groups having 1 to 4 carbon atoms such as methyl, ethyl, propyl, isopropyl, butyl, isobutyl, tert-butyl, and the like.

Examples of an alkyl group substituted with the nitrogen-containing heterocyclic group include the following.

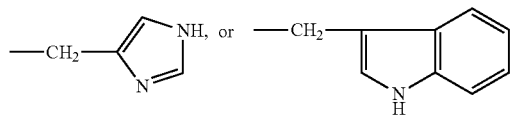

Examples of an alkyl group substituted with the hydroxy group include —CH$_2$OH, —CH(CH$_3$)OH, and the like. Examples of an alkyl group substituted with the carboxy group include —CH$_2$COOH, —CH$_2$CH$_2$COOH, and the like. Examples of an alkyl group substituted with the carbamoyl group include —CH$_2$CONH$_2$, —CH$_2$CH$_2$CONH$_2$, and the like. Examples of an alkyl group substituted with the amino group include —(CH$_2$)$_4$NH$_2$, and the like. Examples of an alkyl group substituted with the guanidino group include —(CH$_2$)$_3$NHC(=NH)NH$_2$ and the like.

Examples of an alkyl group substituted with the alkylsulfanyl group or the arylsulfanyl group include —CH$_2$CH$_2$SCH$_3$, —CH$_2$SH, —CH$_2$S)$_2$, —CH$_2$SR$^{12'}$, and the like. Examples of an alkyl group substituted with the alkoxy group include —CH$_2$OR$^{12'}$ and the like. Examples of an alkyl group substituted with the amido group include —CH$_2$NHCOR$^{12'}$ and the like.

R$^{12'}$ denotes a group other than hydrogen atom and corresponds to a substrate structure of each enzyme. Specifically, it may denote an alkyl group that may have substituent groups, a benzyl group that may have substituent groups, a phenyl group that may have substituent groups, a heterocyclic residual group that may have substituent groups and the like. Additionally, R$^{12'}$ is subordinate concept of R$^{12}$ and thus different from R'.

Examples of the substituent group of the alkyl group that may have substituent groups of R$^{12'}$ include an acyl group, an alkoxycarbonyl group, an amido group, and the like. Further, the alkyl group for R$^{12'}$ is preferably an alkyl group having 1 to 6 carbon atoms.

Examples of the alkyl group for R$^{12}$ include —CH$_3$, —CH$_2$CH$_3$, —CH$_2$CH$_2$CH$_3$, —CH(CH$_3$)$_2$, —CH$_2$CH$_2$CH$_2$CH$_3$, —CH(CH$_3$)CH$_2$CH$_3$, —CH$_2$CH(CH$_3$)$_2$, —C(CH$_3$)$_3$, —CH$_2$CH$_2$R$^{12'}$, and the like. R$^{12'}$ is defined as described above.

Further, examples of the aryl group for R$^{12}$ include a phenyl group and the like.

R$^{13}$ denotes a hydrogen atom, the following group,

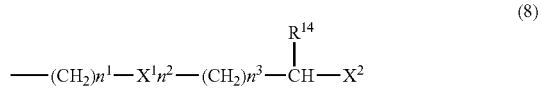

(8)

or the like.

n$^1$ denotes an integer of 0 to 4: n$^2$ denotes 0 or 1: and n$^3$ denotes an integer of 0 to 4. Especially, it is preferable that n$^3$ is 0 or 1. Further, it is also preferable that when n$^2$ is 0, the sum of n$^1$ and n$^3$ is 1 to 3 and when n$^2$ is 1, the sum of n$^1$ and n$^3$ is 0 or 1.

Examples for X$^1$ include an amido group, an alkenyl group, or the like and the X$^2$ alkenyl group is preferably —CH=CH— or the like. Examples for X$^2$ are a carboxy group, an equivalent group of a carboxy group, or the like.

R$^{14}$ denotes a hydrogen atom, a lower alkyl group or the like and examples of the lower alkyl group include those described above. Especially the methyl group and the ethyl group are preferable.

With respect to the alkyl group that may have substituent groups, the above carboxy group and the equivalent group of a carboxy group may include —COOR, —CONR$_2$, —COR, —CN, —NO$_2$, —NHCOR, —OR, —SR, —OCOR, —SO$_3$R, —SO$_2$NR$_2$, and the like. R of these groups denotes a hydrogen atom or an alkyl group and the alkyl group is preferably the lower alkyl group as described above and especially the methyl group is preferable.

Next, the aryl group that may have substituent groups in R$^{10}$ and R$^{11}$ will be described.

Examples of substituent groups of the aryl group that may have substituent groups include an alkyl group that may be substituted with a carboxy group or an equivalent group of a carboxy group, an electron-withdrawing group, a carboxy group, an equivalent group of a carboxy group, and the like.

The aryl group that may have substituent groups is preferable to have a structure containing a carboxy group or an equivalent group thereof bonded to the terminal carbon atom of the aryl group or substituent groups substituted with the aryl group and having 6 to 8 atoms, excluding hydrogen atoms, away from the oxygen atom bonded to phosphorus atom to the terminal of a carboxy group or an equivalent group thereof in the phosphonic acid diester derivative (21).

Examples of the aryl group are a phenyl group and the like.

The phenyl group that may have substituent groups is represented by the following formula.

(9)

Y$^1$ denotes —R', —OR', or an electron-withdrawing group and particularly preferably an electron-withdrawing group. R' denotes hydrogen atom or an alkyl group that may have a double bond and the alkyl group is preferably the lower alkyl group described above and particularly preferably the methyl group or the ethyl group.

Y$^2$ denotes an alkyl group that may be substituted with a carboxy group or an equivalent group of the carboxy group and that may have a double bond, a hydrogen atom, a carboxy group, an equivalent group of a carboxy group or the like. The alkyl group is preferably the same lower alkyl group described above and particularly preferably the methyl group or the ethyl group.

In addition, Y$^1$ and Y$^2$ may be at ortho-, meta-, or para-positions and particularly meta- and para-positions are preferable and para-positions are more preferable.

Further, as shown in the general formulas (14) to (16), two neighboring substituent groups Y$^1$ and Y$^2$ may be bonded to each other to form a ring. R$^{16}$ may denote a hydrogen atom or the above lower alkyl group and particularly preferably a hydrogen atom, a methyl group or an ethyl group.

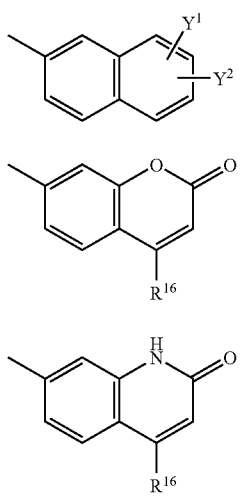

(14)

(15)

(16)

With respect to the aryl group that may have substituent groups, examples of all of the above electron-withdrawing groups include a halogen atom, —COOR', —CONR'$_2$, —COR', —OCOR', —CF$_3$, —CN, —SR', —S(O)R', —SO$_2$R', —SO$_2$NR'$_2$, —PO(OR')$_2$, —NO$_2$, and the like. Examples of the halogen atom include fluorine, chlorine, bromine, and iodine. R' denotes the same as described above.

Further, with respect to the aryl group that may have substituent groups, examples of all of the above carboxy group and the equivalent group of a carboxy group include —COOR", —CONR"$_{12}$, —COR", —CN, —NO$_2$, —NH-COR", —OR", —SR", —OCOR", —SO$_3$R", —SO 2NR"$_2$, and the like. R" denotes a hydrogen atom or an alkyl group that may have a double bond and the alkyl group is preferably the same lower alkyl group as described above.

In the case $R^{11}$ is a phenyl group that may be substituted with $Y^1$, the phosphonic acid diester derivative is preferably the followings.

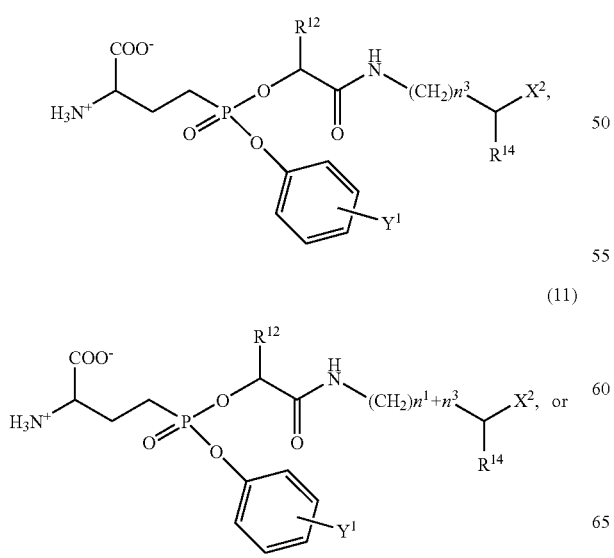

(10)

(11)

(17)

$R^{12}$, $R^{14}$, $X^2$, $Y^1$, $n^1$ and $n^3$ independently denote the same as described above. Further, in the case $R^{11}$ denotes a phenyl group that may be substituted with $Y^1$ and/or $Y^2$, the phosphonic acid diester derivative is preferably the following.

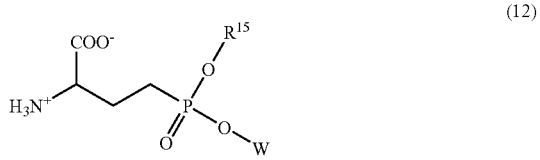

(12)

$R^{15}$ denotes the same lower alkyl group as described above and especially preferably a methyl group or an ethyl group. W denotes a group represented by the following general formulas (13) to (16). $R^{16}$, $Y^1$, and $Y^2$ independently denote the same as described above. In the general formula (13), $Y^2$ is preferable to denote an alkyl group that is substituted with a carboxy group or an equivalent group of a carboxy group, a carboxy group, or an equivalent group of a carboxy group.

(13)

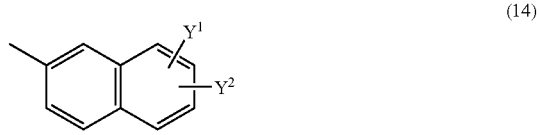

(14)

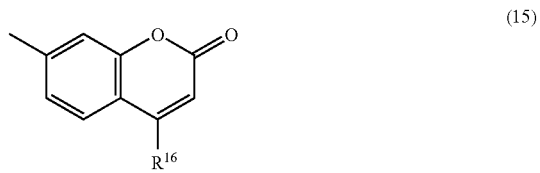

(15)

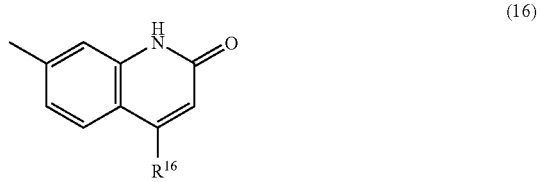

(16)

In the case $R^{10}$ and $R^{11}$ denote a phenyl group that may be substituted with $Y^1$ and/or $Y^2$, the phosphonic acid diester derivative is preferably the following.

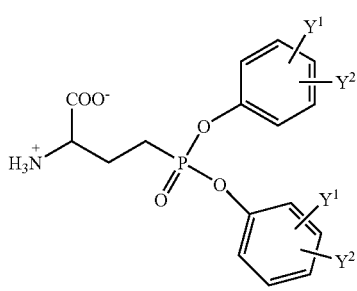

(18)

In this connection, $Y^1$ and $Y^2$ independently denote the same as described above.

Next, a 2-substituted amino-4-phosphonobutanoic acid metal salt (19), an intermediate of a phosphonic acid diester derivative, will be described.

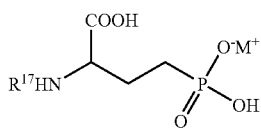

(19)

M denotes an alkali metal. Examples of the alkali metal are lithium, sodium, potassium, and the like and especially sodium is preferable.

$R^{17}$ denotes an alkoxycarbonyl group including an aromatic hydrocarbon group that may have substituent groups and the like. Examples of an alkoxycarbonyl group including an aromatic hydrocarbon group that may have substituent groups include a benzyloxycarbonyl group, a 4-nitrobenzyloxycarbonyl group, a 4-chlorobenzyloxycarbonyl group, a 4-bromobenzyloxycarbonyl group, a 2,4-dichlorobenzyloxycarbonyl group, and the like and especially preferably a benzyloxycarbonyl group and a 4-nitrobenzyloxycarbonyl group.

Next, a 2-substituted amino-4-phosphonobutanoic acid ester (20), an intermediate of a phosphonic acid diester derivative, will be described.

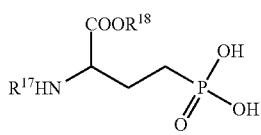

(20)

$R^{18}$ denotes an aromatic hydrocarbon group that may have substituent groups and the like and especially preferably a benzyl group, a 4-nitrobenzyl group, and the like. $R^{17}$ denotes the same as described above.

Next, a method for producing the phosphonic acid diester derivative (1) will be described. The phosphonic acid diester derivative (1) is produced according to a series of reactions including all of the following reaction formulas (1) to (6).

In the production process, the 2-substituted amino-4-phosphonobutanoic acid metal salt (19) is obtained in a form of crystals according to the reaction formula (1). Further, the 2-substituted amino-4-phosphonobutanoic acid ester (20) is obtained in a form of crystals according to the reaction formula (2) by esterifying selectively only the carboxy group in the presence of the phosphonic acid group, followed by crystallization using an ether based solvent.

At first, as shown in reaction formula (1), a reaction of 2-amino-4-phosphonobutanoic acid (21) with a compound (22) is carried out and a reaction of the obtained product with an alkali metal hydroxide (23) is carried out to obtain 2-substituted amino-4-phosphonobutanoic acid metal salt (19).

Reaction formula (1)

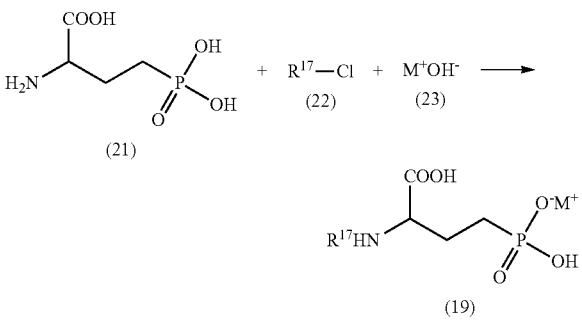

2-Amino-4-phosphonobutanoic acid (21) can be synthesized according to a method described in a Non-patent document (Kosolapoff, G. M. Isomerization of alkyl phosphites. VII. Some derivatives of 2-bromoethanephosphonic acid. J. Am. Chem. Soc. 1948, 70, 1971-1972; Chambers, J. R., Isbell, A. F. A new synthesis of amino phosphonic acids. J. Org. Chem. 1964, 29, 832-836).

In a reaction of 2-amino-4-phosphonobutanoic acid (21) with the compound (22), after 2-amino-4-phosphonobutanoic acid (21) is dissolved in a solvent and the compound (22) and a base are added thereto, the temperature is kept as it is.

As the solvent, such as two-layer solvents of water and an organic solvent that is not mixed with water are used. Examples of the organic solvent to be used are dichloromethane, chloroform, 1,2-dichloroethane, 1,1,1-trichloroethane, tetrachloromethane, benzene, toluene, xylene, pentane, hexane, heptane, octane, cyclopentane, cyclohexane, and ether based solvents and especially ether based solvents are preferable. Examples of the ether based solvents are diethyl ether, diisopropyl ether, tert-butyl methyl ether, dipropyl ether, methyl propyl ether, isopropyl methyl ether, butyl methyl ether, isobutyl methyl ether, methyl pentyl ether, isopentyl methyl ether, cyclopentyl methyl ether, cyclohexyl methyl ether, dibutyl ether and the like.

The temperature for addition of the compound (22) may be a temperature around room temperature or less in order to suppress decomposition of the compound (22) and especially preferably around 0° C. Under such a temperature condition, after the compound (22) is added in 30 minutes to 2 hours, the temperature is kept while the mixture is being stirred until the completion of the reaction is confirmed by a method such as a thin layer chromatographic method. It is kept at a temperature around room temperature, e.g. 25 to 30° C. for 10 to 24 hours.

As the base, an inorganic base such as alkali metal hydroxides, alkali metal carbonates, alkali metal hydrogen carbonates, and the like are employed. Examples of the inorganic base include lithium hydroxide, sodium hydroxide, potassium hydroxide, lithium carbonate, sodium carbonate, potassium carbonate, lithium hydrogen carbonate, sodium hydrogen carbonate, potassium hydrogen carbonate, and the like. The base may be added in the step of dissolving 2-amino-4- phosphonobutanoic acid (21) in a solvent or simultaneously added with the compound (22) or added in both addition steps.

Post-treatment may involve separating a water layer on completion of the reaction and washing the water layer with an ether based solvent that is not mixed with water, if necessary, and acidifying by adding an acid. Examples of the acid include hydrochloric acid, hydrobromic acid, sulfuric acid, and the like.

Next, if necessary vacuum-concentration is carried out, an organic solvent such as acetone or the like is added to the residue, and inorganic salt such as sodium chloride insoluble in the organic solvent is removed by filtration or the like, and successively concentration is carried out to obtain an oil-like crude product containing a product in form of a free phosphonic acid having an amino group moiety protected with $R^{17}$.

The obtained crude product is dissolved in an aqueous solution of an alkali metal hydroxide (23) in an amount for neutralization. Examples of the alkali metal hydroxide (23) include lithium hydroxide, sodium hydroxide, potassium hydroxide, and the like. Thereafter, the aqueous solution dissolving the crude product is concentrated and an organic solvent such as acetone is added to the residue and stirred to isolate the 2-substituted amino-4-phosphonobutanoic acid metal salt (19) in a form of crystals.

Accordingly the amino group of the compound (21) can be protected with a protective group: $R^{17}$. Further, this protected compound is crystallized in form of an alkali metal salt, the 2-substituted amino-4-phosphonobutanoic acid metal salt (19) can be isolated in a high yield.

Next, as shown in reaction formula (2), a reaction of the 2-substituted amino-4-phosphonobutanoic acid metal salt (19) obtained according to the reaction formula (1) with a compound (24) is carried out to obtain a 2-substituted amino-4-phosphonobutanoic acid ester (20).

Reaction formula (2)

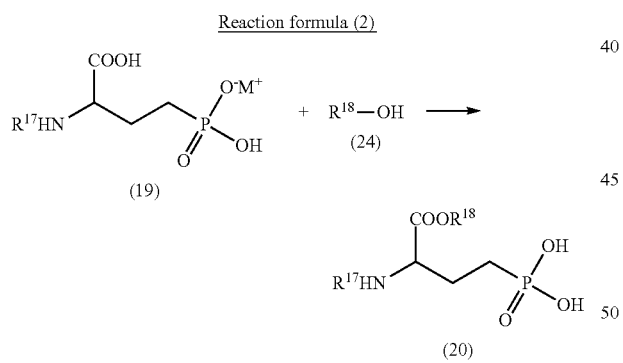

The reaction of the 2-substituted amino-4-phosphonobutanoic acid metal salt (19) with the compound (24) is carried out at a temperature around room temperature in the presence of an acid catalyst in an excess amount. As the acid catalyst, hydrogen chloride or the like is employed.

Next, while stirring is being carried out, the temperature is kept until the completion of the reaction is confirmed by a method such as a thin layer chromatographic method. It is kept at a temperature around room temperature for 12 to 24 hours.

On completion of the reaction, after the excess compound (24) and hydrogen chloride are removed by concentration treatment and the like if necessary, an organic solvent is added to the residue and inorganic salts such as sodium chloride insoluble in the organic solvent are removed by filtration or the like. Examples of the organic solvent to be employed may be ethyl acetate, acetone, ethyl methyl ketone, acetonitrile, tetrahydrofuran, chloroform, dichloromethane, 1,2-dichloroethane, 1,1,1-trichloroethane, and the like. If necessary, after being washed with water, the solution containing the reaction product may be dried with a desiccant such as anhydrous sodium sulfate.

Next, an ether based solvent is added to the solution containing the reaction product and seed crystals are added and stirred and kept at a proper temperature and accordingly, the 2-substituted amino-4-phosphonobutanoic acid ester (20) can be obtained as crystals. Additionally, before the ether based solvent is added, it is preferable to remove the solvent by vacuum concentration or the like.

Examples of the ether based solvent may be diethyl ether, diisopropyl ether, tert-butyl methyl ether, dipropyl ether, 1,2-dimethoxyethane, methyl propyl ether, isopropyl methyl ether, butyl methyl ether, isobutyl methyl ether, methyl pentyl ether, isopentyl methyl ether, cyclopentyl methyl ether, cyclohexyl methyl ether, tetrahydrofuran, dibutyl ether, tetrahydropyran, and the like.

Accordingly, in the 2-substituted amino-4-phosphonobutanoic acid metal salt (19), the carboxy group alone is selectively esterified and protected with a protective group: $R^{18}$, while the phosphonic acid group is kept as being free. Further, the 2-substituted amino-4-phosphonobutanoic acid ester (20) is crystallized in an ether based solvent to isolate the 2-substituted amino-4-phosphonobutanoic acid ester (20) in a high yield.

The seed crystals of the 2-substituted amino-4-phosphonobutanoic acid ester (20) can be obtained by adding a proper amount of the same ether based solvent as described above to the crude product, heating it to almost the boiling point and cooling.

Next, as shown in a reaction formula (3), the 2-substituted amino-4-phosphonobutanoic acid ester (20) obtained according to reaction formula (2) is halogenated to obtain a compound (25).

Reaction formula (3)

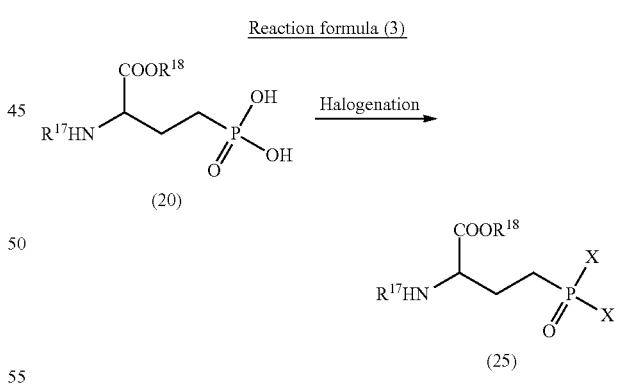

Halogenation of the 2-substituted amino-4-phosphonobutanoic acid ester (20) is carried out by causing a reaction of the 2-substituted amino-4-phosphonobutanoic acid ester (20) with a halogenation agent in the presence of a catalyst.

As the catalyst, N,N-dimethylformamide or the like may be used. As the solvent, dry solvents such as dichloromethane, chloroform, 1,2-dichloroethane, 1,1,1-trichloroethane, tetrachloromethane, diethyl ether, diisopropyl ether, tert-butyl methyl ether, tetrahydrofuran, and the like may be used. As the halogenation agent, oxalyl chloride, thionyl chloride, phosphorus pentachloride, phosphorus oxychloride and the like may be used. The reaction is carried out at a temperature around room temperature for 1 hour.

Next, the byproducts such as hydrogen chloride and the excess halogenation agent are removed if necessary, the compound (25) is obtained as a yellow oil-like substance. In this connection, commonly employed techniques can be used for the method of removing the byproducts or the like, and a method of evaporating the byproducts by blowing an inert gas such as argon at room temperature is especially preferable. If the byproducts are completely removed together with the solvent by employing this removal method, the yield of the compound (25) can be improved.

Examples of X include a halogen atom such as fluorine, chlorine, bromine, iodine and the like and especially chlorine is preferable.

Next, as shown in a reaction formula (4), a reaction of the compound (25) obtained according to the reaction formula (3) with a compound (26) is carried out to obtain a compound (27).

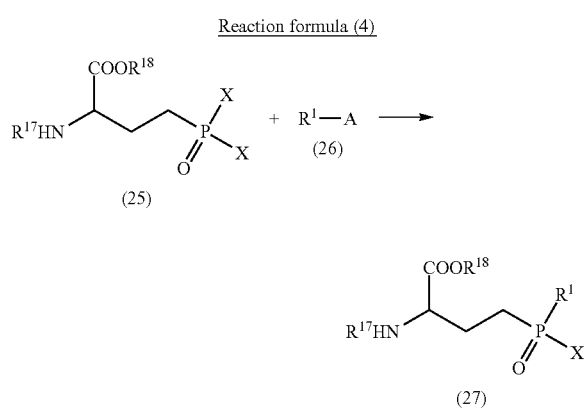

The reaction of the compound (25) with the compound (26) is carried out by dissolving the compound (25) in a solvent, adding the compound (26) thereto, and carrying out the reaction in the presence of an amine base if necessary.

A hydrogen atom or an alkali metal may be used for A of $R^1$-A of the compound (26). Examples of the alkali metal include lithium, sodium, potassium, and the like and especially, lithium is preferable. Examples of amine base to be used are triethylamine, tributylamine, diisopropylethylamine, N-methylpiperidine, N-methylmorpholine, diethylisopropylamine, N-methylimidazole, pyridine, and the like and especially, triethylamine is preferable. Dry dichloromethane solution and the like may be used as the solvent. The reaction is completed after stirring the solvent at around −65° C. for about 30 minute, increasing the temperature slowly to a temperature around room temperature and stirring for about 1 to 3 hours as it is. Accordingly, the compound (27) is obtained as a mixture of diastereomers.

Next, as shown in a reaction formula (5), a reaction of the compound (27) obtained according to the reaction formula (4) with a compound (28) is carried out to obtain a compound (29).

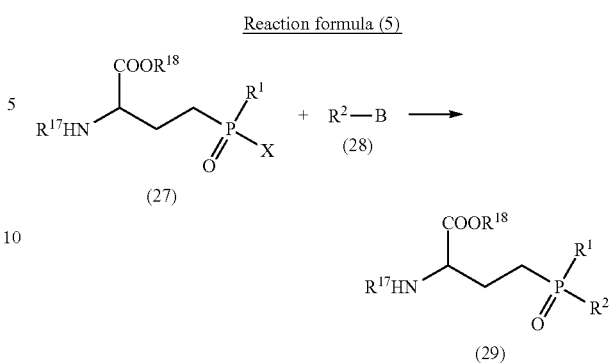

The compound (27) is dissolved in a solvent and the compound (28) and a base, if necessary, are added to carry out the reaction.

A hydrogen atom or an alkali metal may be used for B of $R^2$—B of the compound (28). Examples of the alkali metal include lithium, sodium, potassium, and the like and especially, lithium is preferable. As the solvent, dry dichloromethane solution and the like may be used. As the base, those same as the amine base in the reaction formula (4) may be used.

The compound (28) and the base, if necessary, are added at a temperature around −65° C. After stirring the solvent for about 30 minute after addition, temperature is increased slowly to room temperature and reaction is carried out for about 1 hour until the completion of the reaction is confirmed by a thin layer chromatographic method or the like.

After completion of the reaction, after the organic solvent is removed by vacuum-concentration or the like if necessary, an organic solvent is added to the residue and salts or the like hardly dissolved in the organic solvent are removed by filtration or the like. As the organic solvent, ethyl acetate or acetone is preferable. Next, the diastereomer mixture (29) is obtained as a colorless oil-like substance by a purification method such as column chromatography.

Finally, as shown in a reaction formula (6), the compound (29) obtained according to the reaction formula (5) is deprotected to obtain the phosphonic acid diester derivative (1).

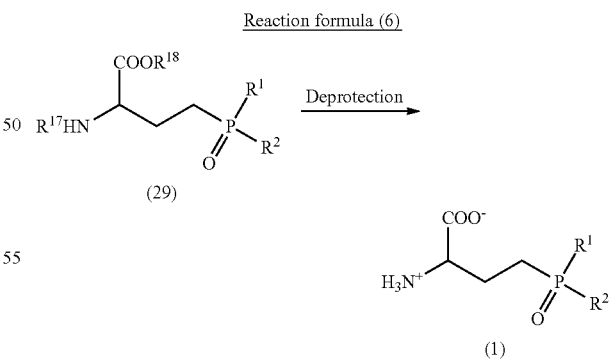

A deprotection method is not particularly limited, however a catalytic hydrogenolysis method, a deprotection method using aluminum chloride, and the like may be employed and especially, the deprotection method using aluminum chloride is preferable.

In the deprotection by the catalytic hydrogenolysis method, in the presence of a catalyst, hydrogen gas is passed through a mixed solution of the compound (29) and a solvent for about 2 hours to deprotect an amino group and a carboxy group.

As the catalyst, a palladium type catalyst, a platinum type catalyst, or the like is employed and as the palladium type catalyst, palladium-carbon, palladium-barium sulfate, or the like may be employed. As the solvent, a mixed solution of water and acetic acid, a solvent mixture of alcohol and water, and the like may be used and as the alcohol, methanol or the like may be used.

Next, after the catalyst and solvent are removed if necessary, the residue is purified by column chromatography or the like. Thereafter, if necessary, vacuum-concentration and freeze drying are carried out to obtain the phosphonic acid diester derivative (1).

Further, in the deprotection method using aluminum chloride, an amino group and a carboxy group are deprotected by causing reaction of the compound (29) with an anisole in a solvent mixed with aluminum chloride.

As the solvent, highly polar solvents such as dry nitromethane may be used. The reaction is carried out by stirring at a temperature around room temperature for 1 hour and thereafter finished by adding water and stirring for about 10 minutes.

Post-treatment is carried out by separating a water layer from the reaction solution after completion of the reaction, washing the water layer with an ether based solvent easy to be separated from water if necessary, and adding methanol. Next, after aluminum hydroxide is removed, if necessary purification is carried out by column chromatography to obtain the phosphonic acid diester derivative (1).

In addition, although crystallization is employed as the purification method of the reaction products in the above-mentioned reaction formulas (1) and (2), extraction, chromatography, precipitation, and the like may be employed in place of the crystallization.

Further, although column chromatography is employed as the purification method of the reaction products in the above reaction formulas (5) and (6), extraction, crystallization, precipitation, and the like may be employed in place of the column chromatography.

EXAMPLES

Example 1

Synthesis of 2-amino-4-[methyl(4-methylphenyl)phosphono]butanoic Acid

After 24.0 g (600 mmol) of sodium hydroxide and 36.6 g (200 mmol) of 2-amino-4-phosphonobutanoic acid were dissolved in a two-layer system solvent mixture of 200 mL of water and 150 mL of ether, 51.2 g (300 mmol) of benzyl chloroformate and 25.2 g (300 mmol) of sodium hydrogen carbonate were added portionwise over 1 hour while being vigorously stirred at 0° C. After the mixture was vigorously stirred at room temperature for 14 hours, it was confirmed that the reaction was finished on the basis of disappearance of 2-amino-4-phosphonobutanoic acid by ninhydrin coloration of thin layer chromatography (TLC) (BuOH/AcOH/$H_2$O=5:2:2). Thereafter, the water layer was separated and washed with 200 mL of ether three times successively, and the solution was acidified by adding 140 mL (840 mmol) of theoretical amount of 6N hydrochloric acid. The aqueous solution was concentrated in reduced pressure, 500 mL of acetone was added to the residue, and insoluble sodium chloride was removed by filtration. The filtrate was concentrated to obtain oily 2-(N-benzyloxycarbonylamino)-4-phosphonobutanoic acid as a crude product. To the crude product, was added 250 mL of an aqueous solution containing 7.2 g (180 mmol) of sodium hydroxide proper for neutralization to adjust the pH to about 3 and the aqueous solution was evaporated to dryness under reduced pressure. The obtained oily substance was mixed with acetone and kept still to obtain 2-(N-benzyloxycarbonylamino)-4-phosphonobutanoic acid monosodium salt (51.8 g, yield 76%) as white powder-like crystals.

$^1$H-NMR (300 MHz, $D_2$O) $\delta_H$ 1.6-1.8 (m, 2H, PCH$_2$CH$_2$), 1.8-2.3 (m, 2H, PCH$_2$CH$_2$), 4.21 (m, 1H, a-CH), 5.13 (s, 2H, OCH$_2$Ph), 7.43 (m, 5H, Ph); $^{31}$P NMR (121 MHz, $D_2$O) $\delta_p$ 25.10.

Next, 226 mL of benzyl alcohol was cooled to 0° C. and 19.5 g (164 mmol) of thionyl chloride was added dropwise. After stirring for 15 minutes, 21.2 g (62.4 mmol) of 2-(N-benzyloxycarbonylamino)-4-phosphonobutanoic acid monosodium salt was added and stirred at room temperature for 20 hours after the ice bath was removed. Completion of the reaction was confirmed by TLC (BuOH/AcOH/$H_2$O=5:2:2, 254 nm). Benzyl alcohol was removed by vacuum distillation at 70° C. using a vacuum pump. The obtained oily residue was extracted by 300 mL of ethyl acetate and insoluble sodium chloride was removed by filtration. After being washed with 50 mL of water three times, the filtrate was dried over anhydrous sodium sulfate. After the solvent was removed by vacuum distillation, 300 mL of diethyl ether was added, seed crystals were added and the mixture stirred vigorously, and the product was crystallized from product mixture was partially dissolved in the ether, benzyl 2-(N-benzyloxycarbonylamino)-4-phosphonobutanoate (21.2 g, yield 84%) was obtained as white powder-like crystals.

$^1$H NMR (300 MHz, acetone-d$_6$) $\delta_H$ 1.7-1.9 (m, 2H, PCH$_2$CH$_2$), 1.9-2.3 (m, 2H, PCH$_2$CH$_2$), 4.38 (m, 1H, a-CH), 5.08 (s, 2H, OCH$_2$Ph), 5.18 (s, 2H, OCH$_2$Ph), 6.9 (d, J=7.8 Hz, 1H, NH), 6.7-7.3 [br s, 2H, P(OH)$_2$], 7.2-7.5 (m, 10H, 2×Ph); $^{31}$P NMR (121 MHz, acetone-d$_6$) $\delta_p$ 29.09. Anal. calcd. for C$_{19}$H$_{22}$NO$_7$P: C, 56.02; H, 5.44; N, 3.44. found: C, 56.08; H, 5.38; N, 3.35. HRMS (FAB, glycerol) calcd for C$_{19}$H$_{23}$NO$_7$P (MH$^+$) 408.1212. found 408.1192.

Additionally, the seed crystals of benzyl 2-(N-benzyloxycarbonylamino)-4-phosphonobutanoate were obtained by adding a proper amount of diisopropyl ether to the crude product, heating to almost boiling point, filtering the supernatant liquid hot, and slowly cooling the filtrate to room temperature.

Next, after 2.01 g (4.93 mmol) of benzyl 2-(N-benzyloxycarbonylamino)-4-phosphonobutanoate was dissolved in 10 mL dry dichloromethane and mixed with a drop of N,N-dimethylformamide, 1.41 g (11.1 mmol) of oxalyl chloride was added at room temperature and reaction was carried out at room temperature as it was for 1 hour. After completion of the reaction, argon gas was passed through the reaction mixture to evaporate and completely remove byproduct hydrogen chloride together with the solvent and accordingly obtain phosphonic acid dichloride as a yellow oil-like substance.

$^1$H NMR (300 MHz, CDCl$_3$) $\delta_H$ 2.1-2.7 (m, 4H, PCH$_2$CH$_2$), 4.53 (m, 1H, a-CH), 5.12 (s, 2H, PhCH$_2$OCON), 5.18 (d, J=12 Hz) and 5.24 (d, J=12 Hz) [2H, PhCH$_2$O], 5.46 (br d, 1H, J=8.1 Hz), 7.3-7.4 (m, 10H, 2×Ph); $^{31}$P NMR (121 MHz, CDCl$_3$) $\delta_p$ 49.0.

After 0.158 g (4.94 mmol) of methanol was added to 20 mL of the dry dichloromethane solution of phosphonic acid dichloride and the solution was cooled to −65° C., 0.5 g (4.94 mmol) of triethylamine was added. After stirring was carried out at −65° C. for 30 minutes, the cooling bath was removed and the temperature was slowly increased to room temperature and stirring was carried out for 1 hour to obtain benzyl 2-(N-benzyloxycarbonylamino)-4-[chloro(methyl)phosphono]butanoate as a mixture of diastereomers.

$^1$H NMR (300 MHz, CDCl$_3$) $\delta_H$ 1.7-2.4 (m, 4H, PCH$_2$CH$_2$), 3.84 (d, 3H, $^3J_{HP}$=13.2 Hz, CH$_3$OP), 4.52 (m, 1H, a-CH), 5.11 (s, 2H, PhCH$_2$OCON), 5.15-5.2 (m, 2H, PhCH$_2$O), 5.5 (br m, 1H, J=8.1 Hz), 7.3-7.4 (m, 10H, 2×Ph); $^{31}$P NMR (121 MHz, CDCl$_3$) $\delta_p$ 44.8.

Next, 0.53 g (4.93 mmol) of 4-methylphenol was added at room temperature to 20 mL of a dry dichloromethane solution containing 4.93 mmol of benzyl 2-(N-benzyloxycarbonylamino)-4-[chloro(methyl)phosphono]butanoate. After the solution was cooled to −65° C., 0.50 g (4.93 mmol) of triethylamine was added. After stirring was carried out at −65° C. for 30 minutes, the cooling bath was removed and the temperature was slowly increased to room temperature and reaction was carried out in that state for 1 hour. After the completion of the reaction was confirmed by TLC (acetone/hexane=1:1), vacuum concentration was carried out and the residue was dissolved in 50 mL of ethyl acetate and the insoluble salt was removed by filtration. The filtrate was vacuum-concentrated and the crude product was purified by flash column chromatography on neutral silica gel 60 N (Kanto Chemical Co., Inc.; No. 37563-79) using a solvent mixture of acetone and hexane at 1:1 ratio and to obtain a diastereomeric mixture of benzyl 2-(N-benzyloxycarbonylamino)-4-[methyl(4-methylphenyl)phosphono]butanoate as a colorless oil-like substance (1.01 g, yield 40%).

$^1$H-NMR (300 MHz, CDCl$_3$) $\delta_H$ 1.8-2.3 (m, 4H, PCH$_2$CH$_2$), 2.3 (s, 3H, CH$_3$), 3.72 (d, $^3J_{HP}$=11.1 Hz, 3H, POCH$_3$), 4.46 (m, 1H, a-CH), 5.10 (s, 2H, OCH$_2$Ph), 5.16 (s, 2H, OCH$_2$Ph), 5.6 (br d, J=6.9 Hz, 1H, NH), 7.0 (d, J=8.4 Hz, 2H) and 7.1 (d, J=8.4 Hz, 2H) (4-methylphenyl), 7.3 (s, 10H, 2×Ph); $^{31}$P NMR (121 MHz, CDCl$_3$) $\delta_p$ 29.34. Anal. calcd. for C$_{27}$H$_{30}$NO$_7$P: C, 63.40; H, 5.91; N, 2.74. found: C, 63.15; H, 5.91; N, 2.81. HRMS (FAB, glycerol) calcd for C$_{27}$H$_{31}$NO$_7$P (MH$^+$) 512.1838. found 512.1837.

Next, 0.70 g (1.37 mmol) of benzyl 2-(N-benzyloxycarbonylamino)-4-[methyl(4-methylphenyl)phosphono]butanoate was dissolved in 30 mL of a solvent mixture of methanol and water at 2:1 and mixed with 270 mg of 5% palladium-carbon and hydrogen gas was introduced for 2 hours. The palladium-carbon was removed by Celite filtration and the filtrate was concentrated under a reduced pressure. The residue was purified by medium pressure reversed-phase column chromatography ODS-S-50B (Yamazen Co., Ltd., Osaka). The column was eluted with a linear gradient of 30 to 60% methanol (6 mL/min flow rate) and the fractions of the compound eluted with 60% methanol were collected. After the elution and purity of the compound were confirmed by TLC (BuOH/AcOH/H$_2$O=5:2:2, ninhydrin coloration), vacuum concentration and freeze drying were carried out to obtain 2-amino-4-[methyl(4-methylphenyl)phosphono]butanoic acid (0.20 g, yield 51%) as a colorless solid.

IR (KBr) $\nu_{max}$ 3600-2300 (br), 1623, 1540, 1508, 1448, 1409, 1365, 1205, 1047, 941, and 833 cm$^{-1}$; $^1$H NMR (300 MHz, D$_2$O) $\delta_H$ 2.1-2.3 (m, 4H, PCH$_2$CH$_2$), 2.31 (s, 3H, CH$_3$), 3.81 (m, 1H, a-CH), 3.85 (d, $^3J_{HP}$=12.3 Hz, 3H, POCH$_3$), 7.11 (d, J=8.1 Hz, 2H) and 7.27 (d, J=7.8 Hz, 2H) (4-methylphenyl); $^{31}$P NMR (121 MHz, D$_2$O) $\delta_p$ 32.53. Anal. calcd. for C$_{12}$H$_{18}$NO$_5$P.0.3H$_2$O: C, 49.25; H, 6.41; N, 4.79. found: C, 49.28; H, 6.32; N, 4.77. HRMS (FAB, glycerol) calcd for C$_{12}$H$_{19}$NO$_5$P (MH$^+$) 288.2567. found 288.1009.

Example 2

Synthesis of 2-amino-4-[(4-methoxyphenyl)(methyl)phosphono]butanoic Acid

At room temperature, 0.66 g (5.32 mmol) of 4-methoxyphenol was added to 20 mL of a dry dichloromethane solution containing 5.35 mmol of benzyl 2-(N-benzyloxycarbonylamino)-4-[chloro(methyl)phosphono]butanoate obtained in the same manner as Example 1. After the solution was cooled to −65° C., 0.55 g (5.39 mmol) of triethylamine was added. After stirring was carried out at −65° C. for 30 minutes, the cooling bath was removed and the temperature was slowly increased to room temperature and reaction was carried out in that state for 1 hour. After the completion of the reaction was confirmed by TLC (acetone/hexane=1:1), vacuum concentration was carried out and the residue was dissolved in 50 mL of ethyl acetate and the insoluble salt was removed by filtration. The filtrate was vacuum-concentrated and the crude product was purified by flash column chromatography on neutral silica gel 60 N using a solvent mixture of acetone and hexane at 1:1 ratio to obtain a diastereomeric mixture of benzyl 2-(N-benzyloxycarbonylamino)-4-[(4-methoxyphenyl)(methyl)phosphono]butanoate as a colorless oil-like substance (0.90 g, yield 32%).

$^1$H-NMR (300 MHz, CDCl$_3$) $\delta_H$ 1.8-2.3 (m, 4H, PCH$_2$CH$_2$), 3.72 (d, $^3J_{HP}$=10.8 Hz, 3H, POCH$_3$), 3.77 (s, 3H, OCH$_3$), 4.47 (m, 1H, a-CH), 5.10 (s, 2H, OCH$_2$Ph), 5.17 (s, 2H, OCH$_2$Ph), 5.5 (br d, J=6.9 Hz, 1H, NH), 6.81 (d, J=9.0 Hz, 2H) and 7.1 (d, J=7.8 Hz, 2H) (4-methoxyphenyl), 7.3 (s, 10H, 2×Ph), $^{31}$P NMR (121 MHz, CDCl$_3$) $\delta_p$ 29.56. Anal. calcd. for C$_{27}$H$_{30}$NO$_8$P: C, 61.48; H, 5.73; N, 2.66. found: C, 61.47; H. 5.82; N, 2.72. HRMS (FAB, glycerol) calcd for C$_{27}$H$_{31}$NO$_8$P (MH$^+$) 528.1787. found 528.1777.

Next, 0.60 g (1.14 mmol) of benzyl 2-(N-benzyloxycarbonylamino)-4-[(4-methoxyphenyl)(methyl)phosphono]butanoate was dissolved in 30 mL of a solvent mixture of methanol and water at 2:1 and mixed with 270 mg of 5% palladium-carbon and hydrogen gas was introduced for 1 hour. Thereafter, the palladium-carbon was removed by Celite filtration and the filtrate was concentrated in reduced pressure. The residue was freeze-dried to obtain 2-amino-4-[(4-methoxyphenyl)(methyl)phosphono]butanoate (0.20 g, yield 58%) as a colorless solid.

IR (KBr) $\nu_{max}$ 3600-2300 (br), 1635, 1597, 1508, 1456, 1409, 1363, 1252, 1207, 1029, 953, and 840 cm$^{-1}$; $^1$H NMR (300 MHz, D$_2$O) $\delta_H$ 2.1-2.3 (m, 4H, PCH$_2$CH$_2$), 3.8-3.9 (m, 7H, a-CH, POCH$_3$ and PhOCH$_3$), 7.03 (d, J=9.3 Hz, 2H) and 7.20 (d, J=8.4 Hz, 2H) (4-methoxyphenyl); $^{31}$P NMR (121 MHz, D$_2$O) $\delta_p$ 32.88; Anal. calcd. for C$_{12}$H$_{18}$NO$_6$P.0.5H$_2$O: C, 46.16; H, 6.13; N, 4.49. found: C, 46.15; H, 6.20; N, 4.45. HRMS (FAB, glycerol) calcd for C$_{12}$H$_{19}$NO$_6$P (MH$^+$) 304.0950. found 304.0945.

Example 3

Synthesis of 2-amino-4-[methyl(phenyl)phosphono]butanoic Acid

In a similar manner for the synthesis of benzyl 2-(N-benzyloxycarbonylamino)-4-[chloro(methyl)phosphono]butanoate in Example 1, benzyl 2-(N-4-nitrobenzyloxycarbonylamino)-4-[chloro(methyl)phosphono]butanoate was obtained.

Next, 0.175 g (1.86 mmol) of phenol was added to 20 mL of a dry dichloromethane solution containing 1.86 mmol of benzyl 2-(N-4-nitrobenzyloxycarbonylamino)-4-[chloro(methyl)phosphono]butanoate at room temperature. After the solution was cooled to 0° C., 0.26 g (2.6 mmol) of triethylamine was added. After stirring was carried out at 0° C. for 30 minutes, the cooling bath was removed and the temperature was slowly increased to room temperature and reaction was carried out in that state for 1 hour. After the completion of the reaction was confirmed by TLC (acetone/hexane=1:1), vacuum concentration was carried out and the residue was dissolved in 50 mL of ethyl acetate and washed successively with 1N hydrochloric acid and an aqueous saturated sodium chloride and thereafter dried over anhydrous sodium sulfate. The solvent was removed by vacuum distillation and the crude product was purified by flash column chromatography on neutral silica gel 60 N using a solvent mixture of acetone and hexane at 1:1 ratio to obtain a diastereomeric mixture of benzyl 2-(N-4-nitrobenzyloxycarbonylamino)-4-[methyl(phenyl)phosphono]butanoate as a colorless oil-like substance (0.48 g, yield 48%).

$^1$H-NMR (300 MHz, CDCl$_3$) $\delta_H$ 1.8-2.4 (m, 4H, PCH$_2$CH$_2$), 3.75 and 3.76 (2×d, $^3J_{HP}$=11.1 Hz, 3H, POCH$_3$), 4.47 (m, 1H, a-CH), 5.20 (m, 4H, 2×OCH$_2$Ph), 5.7 (2×br d, J=7.8 Hz, 1H, NH), 7.1-7.4 (m, 10H, 2×Ph), 7.5 (d, J=7.2 Hz, 2H) and 8.2 (d, J=7.5 Hz, 2H) (4-nitrophenyl); $^{31}$P NMR (121 MHz, CDCl$_3$) $\delta_p$ 29.25 and 29.28. Anal. calcd. for C$_{26}$H$_{27}$N$_2$O$_9$P: C, 57.57; H, 5.02; N, 5.16. found: C, 57.50; H, 4.96; N, 5.13.

Next, 0.57 g (1.05 mmol) of benzyl 2-(N-4-nitrobenzyloxycarbonylamino)-4-[methyl(phenyl)phosphono]butanoate was dissolved in 20 mL of acetic acid and mixed with 210 mg of 10% palladium-carbon and hydrogen gas was introduced for 2 hours. The palladium-carbon was removed by Celite filtration and the filtrate was concentrated in reduced pressure. The residue was purified by medium pressure reversed-phase column chromatography ODS-S-50B. The column was eluted with a linear gradient of 4 to 50% acetonitrile (12 mL/min flow rate) and the fractions of the compound eluted with 5% acetonitrile were collected and the elution and purity of the compound were confirmed by TLC (BuOH/AcOH/H$_2$O=5:2:2, ninhydrin coloration). After vacuum concentration, freeze drying was carried out to obtain 2-amino-4-[methyl(phenyl)phosphono]butanoic acid (0.14 g, yield 48%) as a colorless solid.

IR (KBr) $\nu_{max}$ 3600-2300 (br), 1634, 1593, 1491, 1455, 1403, 1345, 1208, 1045, 936, and 832 cm$^{-1}$; $^1$H NMR (300 MHz, D$_2$O) $\delta_H$ 2.1-2.4 (m, 4H, PCH$_2$CH$_2$), 3.88 (d, $^3J_{HP}$=11.1 Hz, 3H, POCH$_3$), 3.85 (m, 1H, a-CH)), 7.25 (d, J=7.8 Hz, 2H), 7.33 (t, J=7.2 Hz, 1H) and 7.48 (t, J=7.8 Hz, 2H) (phenyl); $^{31}$P NMR (121 MHz, D$_2$O) $\delta_p$ 32.55. Anal. calcd. for C$_{11}$H$_{16}$NO$_5$P.0.6H$_2$O: C, 46.32; H, 6.10; N, 4.93. found: C, 46.36; H, 5.97; N, 5.06. HRMS (FAB, glycerol) calcd for C$_{11}$H$_{17}$NO$_5$P (MH$^+$) 274.0844. found 274.0840.

Example 4

Synthesis of 2-amino-4-[(4-chlorophenyl)(methyl)phosphono]butanoic Acid

4-Chlorophenol 0.59 g (4.59 mmol) was added at room temperature to 20 mL of a dry dichloromethane solution containing 4.59 mmol of benzyl 2-(N-benzyloxycarbonylamino)-4-[chloro(methyl)phosphono]butanoate obtained in the same manner as Example 1. After the solution was cooled to −65° C., 0.46 g (4.59 mmol) of triethylamine was added. After stirring was carried out at −65° C. for 30 minutes, the cooling bath was removed and the temperature was slowly increased to room temperature and reaction was carried out in that state for 1 hour. After the completion of the reaction was confirmed by TLC (acetone/hexane=1:2), vacuum concentration was carried out and the residue was dissolved in 20 mL of acetone and the insoluble salt was removed by filtration. The filtrate was vacuum-concentrated and the crude product was purified by flash column chromatography on neutral silica gel 60 N using a solvent mixture of acetone and hexane at 1:2 to obtain a diastereomeric mixture of benzyl 2-(N-benzyloxycarbonylamino)-4-[(4-chlorophenyl)(methyl)phosphono]butanoate as a colorless oil-like substance (1.45 g, yield 59%).

$^1$H-NMR (300 MHz, CDCl$_3$) $\delta_H$ 1.7-2.4 (m, 4H, PCH$_2$CH$_2$), 3.73 (d, $^3J_{HP}$=11.1 Hz, 3H, POCH$_3$), 4.47 (m, 1H, a-CH), 5.10 (2×s, 2H, OCH$_2$Ph), 5.17 (s, 2H, OCH$_2$Ph), 5.5 (br d, J=8.4 Hz, 1H, NH), 7.09 (d, J=8.1 Hz, 2H) and 7.26 (d, J=8.1 Hz, 2H) (4-chlorophenyl), 7.28-7.40 (m, 10H, 2×Ph); $^{31}$P NMR (121 MHz, CDCl$_3$) $\delta_p$ 29.69. Anal. calcd. for C$_{26}$H$_{27}$ClNO$_7$P: C, 58.71; H, 5.12; N, 2.63. found: C, 58.68; H, 5.10; N, 2.61. HRMS (FAB, glycerol) calcd for C$_{26}$H$_{28}$NO$_7$ClP (MH$^+$) 532.1292. found 532.1300.

Next, 0.73 g (1.37 mmol) of benzyl 2-(N-benzyloxycarbonylamino)-4-[(4-chlorophenyl)(methyl)phosphono]butanoate and 0.89 g (8.22 mmol) of anisole were dissolved in 10 mL of dry nitromethane and mixed with 0.55 g (4.11 mmol) of aluminum trichloride. After stirring was carried out at room temperature for 1 hour, 20 mL of water was added and stirred for 10 minutes. The mixture was washed with 50 mL of ether three times and the water layer was separated and methanol was added to adjust the final concentration of methanol to be 30%. The solution was passed through a short column of neutral silica gel 60N to remove aluminum hydroxide. Without being concentrated, the eluent was purified by medium pressure reversed-phase column chromatography ODS-S-50B. The column was eluted with 40% methanol at a flow rate of 6 mL/min and the fractions of the compound were collected. The elution and purity of the compound were confirmed by TLC (BuOH/AcOH/H$_2$O=5:2:2, ninhydrin coloration). After vacuum concentration, freeze drying was carried out to obtain 2-amino-4-[(4-chlorophenyl)(methyl)phosphono]butanoic acid (0.24 g, yield 57%) as a colorless solid.

IR (KBr) $\nu_{max}$ 3600-2300 (br), 1623, 1595, 1488, 1405, 1358, 1213, 1093, 1045, 928, and 835 cm$^{-1}$; $^1$H NMR (300 MHz, D$_2$O) $\delta_H$ 2.1-2.3 (m, 4H, PCH$_2$CH$_2$), 3.83 (m, 1H, a-CH), 3.86 (d, $^3J_{HP}$=11.4 Hz, 3H, POCH$_3$), 7.21 (d, J=7.8 Hz, 2H) and 7.46 (d, J=8.7 Hz, 2H) (4-chlorophenyl); $^{31}$P NMR (121 MHz, D$_2$O) $\delta_p$ 32.69. Anal. calcd. for C$_{11}$H$_{15}$ClNO$_5$P.0.4H$_2$O: C, 41.96; H, 5.06; N, 4.45. found: C, 42.17; H, 5.03; N, 4.53. HRMS (FAB, glycerol) calcd for C$_{11}$H$_{16}$ClNO$_5$P (MH$^+$) 308.0455. found 308.0466.

Example 5

Synthesis of 2-amino-4-[methyl(4-trifluoromethylphenyl)phosphono]butanoic Acid

4-Trifluoromethylphenol 0.80 g (4.93 mmol) was added at room temperature to 20 mL of a dry dichloromethane solution containing 4.93 mmol of benzyl 2-(N-benzyloxycarbonylamino)-4-[chloro(methyl)phosphono]butanoate obtained in the same manner as Example 1. After the solution was cooled to −65° C., 0.50 g (4.93 mmol) of triethylamine was added. After stirring was carried out at −65° C. for 30 minutes, the cooling bath was removed and the temperature was slowly increased to room temperature and reaction was carried out in that state for 1 hour. After the completion of the reaction was confirmed by TLC (acetone/hexane=1:2), vacuum concentration was carried out and the residue was dissolved in 50 mL of ethyl acetate and the insoluble salt was removed by filtration. The filtrate was vacuum-concentrated and the crude product was purified by flash column chromatography on neutral silica gel 60 N using a solvent mixture of acetone and hexane at 1:2 ratio to obtain a diastereomeric mixture of benzyl 2-(N-benzyloxycarbonylamino)-4-[methyl(4-trifluoromethylphenyl)phosphono]butanoate as a colorless oil-like substance (1.50 g, yield 54%).

¹H-NMR (300 MHz, CDCl₃) $\delta_H$ 1.8-2.3 (m, 4H, PCH₂CH₂), 3.75 (d, $^3J_{HP}$=11.1 Hz, 3H, POCH₃), 4.49 (m, 1H, a-CH), 5.10 (2×s, 2H, OCH₂Ph), 5.18 (s, 2H, OCH₂Ph), 5.5 (br d, J=6.9 Hz, 1H, NH), 7.26 (d, J=8.4 Hz, 2H) and 7.58 (d, J=8.4 Hz, 2H) (4-trifluoromethylphenyl), 7.3 (s, 10H, 2×Ph); ³¹P NMR (121 MHz, CDCl₃) $\delta_p$ 29.83. Anal. calcd. for $C_{27}H_{27}F_3NO_7P$: C, 57.35; H, 4.81; N, 2.48. found: C, 57.25; H, 4.77; N, 2.50. HRMS (FAB, glycerol) calcd for $C_{27}H_{28}F_3NO_7P$ (MH⁺) 566.1556. found 566.1546.

Next, 1.40 g (2.48 mmol) of benzyl 2-(N-benzyloxycarbonylamino)-4-[methyl(4-trifluoromethylphenyl)phosphono]butanoate and 1.61 g (14.9 mmol) of anisole were dissolved in 10 mL of dry nitromethane and mixed with 0.99 g (7.44 mmol) of aluminum trichloride at room temperature. After stirring was carried out at room temperature for 1 hour, 20 mL of water was added and stirred for 10 minutes. The mixture was washed with 50 mL of ether three times and the water layer was separated, and methanol was added to the final concentration of methanol to be 30%. The solution was passed through a short column of neutral silica gel 60N to remove aluminum hydroxide. Without being concentrated, the effluent was purified by medium pressure reversed-phase column chromatography ODS-S-50B. The column was eluted with a linear gradient of 30 to 60% methanol (flow rate of 6 mL/min) and the fractions containing the compound eluted at 60% methanol were collected. The elution and purity of the compound were confirmed by TLC (BuOH/AcOH/H₂O=5:2:2, ninhydrin coloration). After vacuum concentration, freeze drying was carried out to obtain 2-amino-4-[methyl(4-trifluoromethylphenyl)phosphono]butanoic acid (0.53 g, yield 63%) as a colorless solid.

IR (KBr) $\nu_{max}$ 3600-2300 (br), 1646, 1616, 1516, 1403, 1338, 1225, 1174, 1121, 1070, 1047, 933, and 850 cm⁻¹; ¹H NMR (300 MHz, D₂O) $\delta_H$ 2.1-2.4 (m, 4H, PCH₂CH₂), 3.85 (m, 1H, a-CH), 3.89 (2×d, $^3J_{HP}$=11.4 Hz, 3H, POCH₃), 7.41 (d, J=8.4 Hz, 2H) and 7.80 (d, J=8.7 Hz, 2H) (4-trifluoromethylphenyl); ³¹P NMR (121 MHz, D₂O) $\delta_p$ 32.58. Anal. calcd. for $C_{12}H_{15}F_3NO_5P\cdot0.8H_2O$: C, 40.53; H, 4.70; N, 3.94. found: C, 40.63; H, 4.41; N, 4.20. HRMS (FAB, glycerol) calcd for $C_{12}H_{16}F_3NO_5P$ (MH⁺) 342.0178. found 342.0709.

Example 6

Synthesis of 2-amino-4-[(4-cyanophenyl)(methyl)phosphono]butanoic Acid

4-Cyanophenol 0.60 g (5.01 mmol) was added at room temperature to 20 mL of a dry dichloromethane solution containing 5.01 mmol of benzyl 2-(N-benzyloxycarbonylamino)-4-[chloro(methyl)phosphono]butanoate obtained in the same manner as Example 1. After the solution was cooled to −20° C., 0.51 g (5.01 mmol) of triethylamine was added. After stirring was carried out at −20° C. for 30 minutes, the cooling bath was removed and the temperature was slowly increased to room temperature and reaction was carried out in that state overnight. After the completion of the reaction was confirmed by TLC (acetone/hexane=2:3), vacuum concentration was carried out and the residue was dissolved in 20 mL of acetone and the insoluble salt was removed by filtration. The filtrate was vacuum-concentrated and the crude product was purified by flash column chromatography on neutral silica gel 60 N using a solvent mixture of acetone and hexane at 2:3 ratio to obtain a diastereomeric mixture of benzyl 2-(N-benzyloxycarbonylamino)-4-[(4-cyanophenyl)(methyl)phosphono]butanoate as a light-yellow oily substance (1.0 g, yield 38%).

¹H-NMR (300 MHz, CDCl₃) $\delta_H$ 1.8-2.4 (m, 4H, PCH₂CH₂), 3.76 (d, $^3J_{HP}$=11.4 Hz, 3H, POCH₃), 4.49 (m, 1H, a-CH), 5.10 (2×s, 2H, OCH₂Ph), 5.18 (s, 2H, OCH₂Ph), 5.46 (br d, J=6.6 Hz, 1H, NH), 7.3 (d, J=7.5 Hz, 2H) and 7.60 (2×d, J=8.4 Hz) (4-cyanophenyl), 7.4 (s, 10H, 2×Ph); ³¹P NMR (121 MHz, CDCl₃) $\delta_p$ 30.05. Anal. calcd. for $C_{27}H_{27}N_2O_7P$: C, 62.07; H, 5.21; N, 5.36. found: C, 61.93; H, 5.15; N, 5.47.

Next, 0.95 g (1.82 mmol) of benzyl 2-(N-benzyloxycarbonylamino)-4-[(4-cyanophenyl)(methyl)phosphono]butanoate and 1.18 g (10.9 mmol) of anisole were dissolved in 10 mL of dry nitromethane and mixed with 0.73 g (5.46 mmol) of aluminum trichloride at room temperature. After stirring was carried out at room temperature for 1 hour, 20 mL of water was added and stirred for 10 minutes. The mixture was washed with 50 mL of an ether three times and a water layer was separated, and methanol was added to adjust the final concentration of methanol to be 30%. The solution was passed through a short column of neutral silica gel 60N to remove aluminum hydroxide. Without being concentrated, the effluent was purified by medium pressure reversed-phase column chromatography ODS-S-50B. The column was eluted with a linear gradient of 30 to 60% methanol at a flow rate of 6 mL/min and the fractions containing the compound eluted at 45% methanol were collected. The elution and purity of the compound were confirmed by TLC (BuOH/AcOH/H₂O=5:2:2, ninhydrin coloration). After vacuum concentration, freeze drying was carried out to obtain 2-amino-4-[(4-cyanophenyl)(methyl)phosphono]butanoic acid (0.38 g, yield 70%) as a colorless solid.

IR (KBr) $\nu_{max}$ 3600-2300 (br), 2231, 1647, 1604, 1500, 1412, 1360, 1225, 1176, 1105, 1045, 926, and 837 cm⁻¹; ¹H NMR (300 MHz, D₂O) $\delta_H$ 2.1-2.4 (m, 4H, PCH₂CH₂), 3.82 (m, 1H, a-CH), 3.88 (d, $^3J_{HP}$=11.4 Hz, 3H, POCH₃), 7.39 (d, J=8.7 Hz, 2H) and 7.83 (d, J=8.1 Hz, 2H) (4-cyanophenyl); ³¹P NMR (121 MHz, D₂O) $\delta_p$ 32.61. Anal. calcd. for $C_{12}H_{15}N_2O_5P\cdot0.3H_2O$: C, 47.47; H, 5.18; N, 9.23. found: C, 47.56; H, 5.09; N, 9.24. HRMS (FAB, glycerol) calcd for $C_{12}H_{16}N_2O_5P$ (MH⁺) 299.0797. found 299.0789.

Example 7

Synthesis of 2-amino-4-[methyl(4-nitrophenyl)phosphono]butanoic Acid

4-Nitrophenol 0.68 g (4.91 mmol) was added at room temperature to 20 mL of a dry dichloromethane solution containing 4.91 mmol of benzyl 2-(N-benzyloxycarbonylamino)-4-[chloro(methyl)phosphono]butanoate obtained in the same manner as Example 1. After the solution was cooled to −20° C., 0.50 g (4.91 mmol) of triethylamine was added. After stirring was carried out at −20° C. for 30 minutes, the cooling bath was removed and the temperature was slowly increased to room temperature, and reaction was carried out in that state overnight. After the completion of the reaction was confirmed by TLC (acetone/hexane=1:2), vacuum concentration was carried out and the residue was dissolved in 20 mL of acetone and the insoluble salt was removed by filtration. The filtrate was vacuum-concentrated and the crude product was purified by flash column chromatography on neutral silica gel 60 N using a solvent mixture of acetone and hexane at 1:2 ratio to obtain a diastereomeric mixture of benzyl 2-(N-benzyloxycarbonylamino)-4-[methyl(4-nitrophenyl)phosphono]butanoate as a light-yellow oily substance (1.2 g, yield 45%).

$^1$H-NMR (300 MHz, CDCl$_3$) $\delta_H$ 1.8-2.3 (m, 4H, PCH$_2$CH$_2$), 3.77 (d, $^3$J$_{HP}$=11.1 Hz, 3H, POCH$_3$), 4.5 (m, 1H, a-CH), 5.10 (m, 2H) and 5.18 (m, 2H) (2×OCH$_2$Ph), 5.5 (d, J=6.9 Hz, 1H, NH), 7.31 (d, J=9.3 Hz, 2H) and 8.20 (d, J=9.0 Hz, 2H) (4-nitrophenyl), 7.3 (s, 10H, 2×Ph); $^{31}$P NMR (121 MHz, CDCl$_3$) $\delta_p$ 30.20. Anal. calcd. for C$_{26}$H$_{27}$N$_2$O$_9$P: C, 57.57; H, 5.02; N, 5.16. found: C, 57.35; H, 5.11; N, 5.17. HRMS (FAB, glycerol) calcd for C$_{26}$H$_{28}$N$_2$O$_9$P (MH$^+$) 543.1532. found 543.1537.

Next, 0.85 g (1.57 mmol) of benzyl 2-(N-benzyloxycarbonylamino)-4-[methyl(4-nitrophenyl)phosphono]butanoate and 1.02 g (9.42 mmol) of anisole were dissolved in 10 mL of dry nitromethane and mixed with 0.63 g (4.71 mmol) of aluminum trichloride. After stirring was carried out at room temperature for 1 hour, 20 mL of water was added and stirred for 10 minutes. The mixture was washed with 50 mL of ether three times and the water layer was separated, and methanol was added to adjust the final concentration of methanol to be 30%. The solution was passed through a short column of neutral silica gel 60N to remove aluminum hydroxide. Without being concentrated, 30 mL of the effluent was purified by medium pressure reversed-phase column chromatography ODS-S-50B. The column was eluted with a linear gradient of 30 to 60% methanol at a flow rate of 6 mL/min and the fractions containing the compound eluted at 48% methanol were collected. The elution and purity of the compound were confirmed by TLC (BuOH/AcOH/H$_2$O=5:2:2, ninhydrin coloration). After vacuum concentration, freeze drying was carried out to obtain 2-amino-4-[methyl(4-nitrophenyl)phosphono]butanoic acid (0.35 g, yield 70%) as a colorless solid.

IR (KBr) $v_{max}$ 3600-2300 (br), 2231, 1629, 1590, 1490, 1411, 1342, 1292, 1223, 1164, 1108, 1045, 931, and 860 cm$^{-1}$; $^1$H NMR (300 MHz, D$_2$O) $\delta_H$ 2.1-2.4 (m, 4H, PCH$_2$CH$_2$), 3.88 (m, 1H, a-CH), 3.91 (d, $^3$J$_{HP}$=11.4 Hz, 3H, POCH$_3$), 7.44 (d, J=8.7 Hz, 2H) and 8.33 (d, J=9.0 Hz, 2H) (4-nitrophenyl); $^{31}$P NMR (121 MHz, D$_2$O) $\delta_p$ 32.63. Anal. calcd. for C$_{11}$H$_{15}$N$_2$O$_7$P.1.5H$_2$O: C, 38.27; H, 5.26; N, 8.11. found: C, 38.25; H, 5.05; N, 8.20. HRMS (FAB, glycerol) calcd for C$_{11}$H$_{16}$N$_2$O$_7$P (MH$^+$) 319.0695. found 319.0703.

The structures of the compounds of Examples 1 to 7 are shown in Table 1

TABLE 1

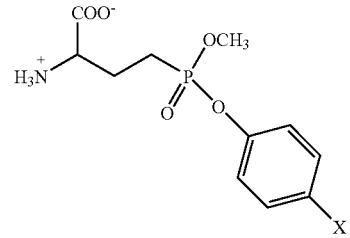

| Example | Substituent group: X |
|---|---|
| 1 | CH$_3$ |
| 2 | OCH$_3$ |
| 3 | H |
| 4 | Cl |
| 5 | CF$_3$ |
| 6 | CN |
| 7 | NO$_2$ |

Example 8

Synthesis of 2-amino-4-[methyl(4-methylumbelliferyl)phosphono]butanoic Acid

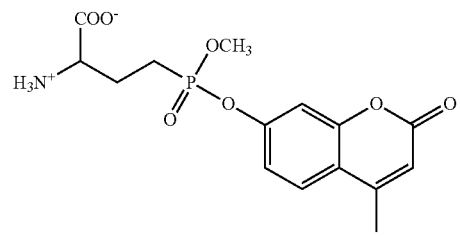

4-Methylumbelliferone 0.87 g (4.93 mmol) was added at room temperature to 20 mL of a dry dichloromethane solution containing 4.93 mmol of benzyl 2-(N-benzyloxycarbonylamino)-4-[chloro(methyl)phosphono]butanoate obtained in the same manner as Example 1. After the solution was cooled to −65° C., 0.49 g (4.83 mmol) of triethylamine was added. After stirring was carried out at −65° C. for 30 minutes, the cooling bath was removed and the temperature was slowly increased to room temperature and reaction was carried out for 1 hour in that state. After the completion of the reaction was confirmed by TLC (EtOAc/hexane=3:1), vacuum concentration was carried out and the residue was dissolved in 50 mL of ethyl acetate and the insoluble salt was removed by filtration. The filtrate was vacuum-concentrated and the crude product was purified by flash column chromatography on neutral silica gel 60 N using a solvent mixture of ethyl acetate and hexane at 3:1 ratio to obtain a diastereomeric mixture of benzyl 2-(N-benzyloxycarbonylamino)-4-[methyl(4-methylumbelliferyl)phosphono]butanoate as a light-yellow oily substance (1.30 g, yield 46%).

$^1$H-NMR (300 MHz, CDCl$_3$) $\delta_H$ 1.8-2.3 (m, 4H, PCH$_2$CH$_2$), 2.42 (s, 3H, CH$_3$), 3.77 (d, $^3$J$_{HP}$=11.1 Hz, 3H, POCH$_3$), 4.49 (m, 1H, a-CH), 5.11 (s, 2H, OCH$_2$Ph), 5.19 (s, 2H, OCH$_2$Ph), 5.5 (br d, J=6.9 Hz, 1H, NH), 6.25 (s, 1H, 3'-H), 7.14 (s, 1H, 8'-H), 7.16 (d, 1H, J=9 Hz, 5'-H), 7.3-7.4 (s, 10H, 2×Ph), 7.53 (d, 1H, J=8.4 Hz); $^{31}$P NMR (121 MHz, CDCl$_3$) $\delta_p$ 30.07. Anal. calcd. for C$_{30}$H$_{30}$NO$_9$P: C, 62.18; H, 5.22; N, 2.42. found C, 62.09; H, 5.25; N, 2.54. HRMS (FAB, glycerol) calcd. for C$_{30}$H$_{31}$NO$_9$P (MH$^+$) 580.1737. found 580.1727.

Next, 0.70 g (1.21 mmol) of benzyl 2-(N-benzyloxycarbonylamino)-4-[methyl(4-methylumbelliferyl)phosphono]butanoate and 0.79 g (7.26 mmol) of anisole were dissolved in 10 mL of dry nitromethane and mixed with 0.48 g (3.63 mmol) of aluminum trichloride at room temperature. After stirring was carried out at room temperature for 1 hour, 20 mL of water was added and stirred for 10 minutes. The mixture was washed with 50 mL of ether three times and the water layer was separated, and methanol was added to adjust the final concentration of methanol to be 30%. The solution was passed through a short column of neutral silica gel 60N to remove aluminum hydroxide. Without being concentrated, 30 mL of the effluent was purified by medium pressure reversed-phase column chromatography ODS-S-50B. The column was eluted with a linear gradient of 30 to 60% methanol at a flow rate of 6 mL/min and the fractions containing the compound eluted at 60% methanol were collected. The elution and purity of the compound were confirmed by TLC (BuOH/AcOH/H$_2$O=5:2:2, ninhydrin coloration). After vacuum concentration, freeze drying was carried out to obtain 2-amino-4-[methyl(4-methylumbelliferyl)phosphono]butanoic acid (0.21 g, yield 49%) as a colorless solid.

IR (KBr) $\nu_{max}$ 3600-2300 (br), 1733, 1716, 1612, 1506, 1446, 1390, 1270, 1230, 1137, 1070, 1043, 989, 920, and 833 cm$^{-1}$; $^1$H NMR (300 MHz, D$_2$O) $\delta_H$ 2.1-2.4 (m, 4H, PCH$_2$CH$_2$), 2.49 (s, 3H, CH$_3$), 3.86 (m, 1H, a-CH), 3.91 (2×d, $^3J_{HP}$=11.4 Hz, 3H, POCH$_3$), 6.4 (s, 1H, 3'-H), 7.27 (d, J=8.1 Hz, 1H, 5'-H), 7.28 (s, 1H, 8'-H), 7.84 (d, J=8.1 Hz, 1H, 6'-H); $^{31}$P NMR (121 MHz, D$_2$O) $\delta_p$ 32.69. Anal. calcd. for C$_{15}$H$_{18}$NO$_7$P.0.3H$_2$O: C, 49.95; H, 5.20; N, 3.88. found: C, 49.86; H, 5.14; N, 3.84. HRMS (FAB, glycerol) calcd for C$_{15}$H$_{19}$NO$_7$P (MH$^+$) 356.0899. found 356.0904.

Example 9

Synthesis of 2-amino-4-[butyl(phenyl)phosphono]butanoic Acid

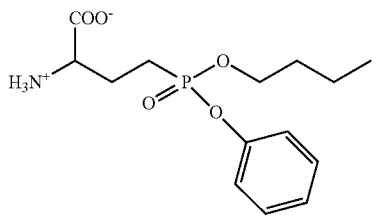

1-Butanol 0.35 g (4.72 mmol) was added at room temperature to 20 mL of a dry dichloromethane solution containing 4.91 mmol of phosphonic acid dichloride obtained in the same manner as Example 1. After the solution was cooled to −65° C., 0.47 g (4.66 mmol) of triethylamine was added. After stirring was carried out at −65° C. for 30 minutes, the cooling bath was removed and the temperature was slowly increased to room temperature and reaction was carried out for 1 hour in that state to obtain a crude product of monobutylmonochlorophosphonic acid as a mixture of diastereomers.

$^1$H NMR (300 MHz, CDCl$_3$) $\delta_H$ 0.86-0.96 (m, 3H, OCH$_2$CH$_2$CH$_2$CH$_3$) d$_H$ 1.3-2.6 (m, 8H, PCH$_2$CH$_2$ and OCH$_2$CH$_2$CH$_2$CH$_3$), 3.9-4.3 (m, 2H, OCH$_2$CH$_2$CH$_2$CH$_3$), 4.5 (m, 1H, a-CH), 5.0-5.2 (m, 4H, 2×PhCH$_2$O), 5.4 (br m, 1H, NH), 7.2-7.4 (m, 10H, 2×Ph); $^{31}$P NMR (121 MHz, CDCl$_3$) $\delta_p$ 43.1.

Next, 0.46 g (4.91 mmol) of phenol was added at room temperature to 20 mL of a dry dichloromethane solution containing 4.91 mmol of monobutylmonochlorophosphonic acid. After the solution was cooled to −65° C., 0.50 g (4.91 mmol) of triethylamine was added. After stirring was carried out at −65° C. for 30 minutes, the cooling bath was removed the temperature was slowly increased to room temperature and reaction was carried out for 1 hour in that state. After the completion of the reaction was confirmed by TLC (EtOAc/hexane=2:3), vacuum concentration was carried out and the residue was dissolved in 30 mL of acetone and the insoluble salt was removed by filtration. The filtrate was vacuum-concentrated and the crude product was purified by flash column chromatography on neutral silica gel 60 N using a solvent mixture of ethyl acetate and hexane at 2:3 ratio obtain a diastereomeric mixture of benzyl 2-(N-benzyloxycarbonylamino)-4-[butyl(phenyl)phosphono]butanoate as a colorless oily substance (0.76 g, yield 29%).

$^1$H-NMR (300 MHz, CDCl$_3$) $\delta_H$ 0.88 (t, J=7.2 Hz, 3H, OCH$_2$CH$_2$CH$_2$CH$_3$), 1.2-1.4 (m, 2H, OCH$_2$CH$_2$CH$_2$CH$_3$), 1.5-1.6 (m, 2H, OCH$_2$CH$_2$CH$_2$CH$_3$), 1.8-2.3 (m, 4H, PCH$_2$CH$_2$), 4.1 (m, 2H, OCH$_2$CH$_2$CH$_2$CH$_3$), 4.5 (m, 1H, a-CH), 5.1 (m, 2H, PhCH$_2$OCON), 5.2 (m, 2H, PhCH$_2$O), 5.5 (br d, J=7.8 Hz, 1H), 7.1-7.3 (m, 15H, 3×Ph); $^{31}$P NMR (121 MHz, CDCl$_3$) $\delta_p$ 28.0. Anal. calcd. for C$_{29}$H$_{34}$NO$_7$P: C, 64.55; H, 6.35; N, 2.60. found: C, 64.55; H, 6.36; N, 2.64.

Next, 0.64 g (1.19 mmol) of benzyl 2-(N-benzyloxycarbonylamino)-4-[butyl(phenyl)phosphono]butanoate was dissolved in 20 mL of a solvent mixture of methanol and water at 3:1 and mixed with 200 mg of 5% palladium-carbon and hydrogen gas was introduced for 75 minutes. The palladium-carbon was removed by Celite filtration and the filtrate was vacuum-concentrated. The residue was purified by medium pressure reversed-phase column chromatography ODS-S-50B. The column was eluted with a linear gradient of 30 to 60% methanol at a flow rate of 6 mL/min, and the fractions containing the compound eluted at 60% methanol were collected. The elution and purity of the compound were confirmed by TLC (BuOH/AcOH/H$_2$O=5:2:2, ninhydrin coloration). After vacuum concentration, freeze drying was carried out to obtain 2-amino-4-[butyl(phenyl)phosphono]butanoic acid (0.28 g, yield 75%) as a colorless solid.

IR (KBr) $\nu_{max}$ 3600-2300 (br), 1623, 1597, 1541, 1491, 1408, 1363, 1290, 1207, 1059, 1024, 939, and 765 cm$^{-1}$; $^1$H NMR (300 MHz, D$_2$O) $\delta_H$ 0.87 (t, 3H, OCH$_2$CH$_2$CH$_2$CH$_3$), 1.3-1.4 (m, 2H, OCH$_2$CH$_2$CH$_2$CH$_3$), 1.6-1.7 (m, 2H, OCH$_2$CH$_2$CH$_2$CH$_3$), 2.1-2.3 (m, 4H, PCH$_2$CH$_2$), 3.8 (m, 1H, a-CH), 4.2 (m, 2H, OCH$_2$CH$_2$CH$_2$CH$_3$), 7.23 (d, J=8.1 Hz, 2H), 7.31 (t, J=7.2 Hz, 1H) and 7.46 (t, J=7.8 Hz, 2H) (phenyl); $^{31}$P NMR (121 MHz, D$_2$O) $\delta_p$ 31.1. Anal. calcd. for C$_{14}$H$_{22}$NO$_5$P.0.4H$_2$O: C, 52.14; H, 7.13; N, 4.34. found: C, 52.25; H, 7.15; N, 4.60.

Example 10

Synthesis of 2-amino-4-[1-[N-(carboxymethyl)carbamoyl]propyl (phenyl)phosphono]butanoic Acid

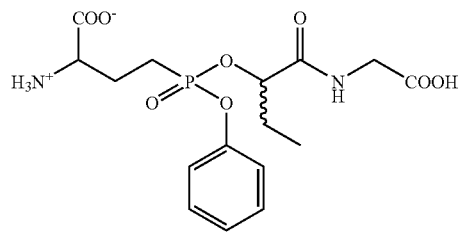

1.50 g (13.6 mmol) of lithium 2-hydroxybutanoate, 4.60 g (13.6 mmol) of glycine benzyl ester p-toluenesulfonic acid salt, and 1.84 g (1.36 mmol) of 1-hydroxybenzotriazole monohydrate (HOBt) were added to 80 mL of acetonitrile and stirred at room temperature for 20 minutes. The mixture was further mixed with 2.61 g (13.6 mmol) of 1-(3-dimethylaminopropyl)-3-ethylcarbodiimide hydrochloride (EDC) and stirred at room temperature overnight. After the reaction mixture was filtered, the filtrate was vacuum-concentrated and the residue was dissolved in 200 mL of ethyl acetate. Washing with 1N hydrochloric acid and an aqueous solution saturated sodium hydrogen carbonate was carried out successively and drying over anhydrous sodium sulfate was carried out. After the solvent as removed by distillation, the residue was purified by flash column chromatography on silica gel (No. 9385, Merck) using a solvent mixture of hexane and ethyl acetate at 1:2 ratio to obtain N-(2-hydroxybutanoyl)glycine benzyl ester as a colorless oily substance (1.67 g, yield 49%).

$^1$H-NMR (300 MHz, CDCl$_3$) $\delta_H$ 0.99 (t, J=7.5 Hz, 3H, CH$_3$CH$_2$), 1.70 (ddq, J=7.2, 7.2 and 15 Hz, 1H) and 1.89 (ddt, J=4.2, 7.2 and 15 Hz, 1H) (CH$_3$CH$_2$), 4.08 (dd, J=5.6 and 18 Hz, 1H, NHCH$_2$CO), 4.14 (dd, J=3.9 and 7.5 Hz, 1H, CH), 4.16 (dd, J=5.7 and 18 Hz, 1H, NHCH$_2$CO), 7.10 (br t, 1H, NH), 7.3-7.4 (s, 5H, Ph). HRMS (FAB, glycerol) calcd. for C$_{13}$H$_{18}$NO$_4$ (MH$^+$) 252.1236. found: 252.1232.

Next, 0.44 g (4.72 mmol) of phenol was added at room temperature to 20 mL of a dry dichloromethane solution containing 4.82 mmol of phosphonic acid dichloride obtained in the same manner as Example 1. After the solution was cooled to −65° C., 0.49 g (4.82 mmol) of triethylamine was added. After stirring was carried out at −65° C. for 30 minutes, the cooling bath was removed and the temperature was slowly increased to room temperature and reaction was carried out for 1 hour in that state to obtain a solution of monophenyl-monochlorophosphonic acid (a diastereomer mixture, $\delta_p$=39.37). The solution was further mixed with 1.21 g (4.82 mmol) of N-(2-hydroxybutanoyl)glycine benzyl ester and cooled to −65° C. Further, 0.49 g (4.82 mmol) of triethylamine was added, and reaction was carried out at −65° C. for 30 minutes and further at room temperature for 1 hour. After the completion of the reaction was confirmed by TLC (acetone/hexane=1:2), vacuum concentration was carried out and the residue was dissolved in 40 mL of ethyl acetate and the insoluble salt was removed by filtration. The filtrate was vacuum-concentrated and the crude product was purified by flash column chromatography on neutral silica gel 60 N using a solvent mixture of acetone and hexane at 1:3 ratio to obtain a four kinds diastereomeric mixture of benzyl 2-(N-benzyloxycarbonylamino)-4-[1-[N-(benzyloxycarbonylmethyl)carbamoyl]propyl(phenyl)phosphono]butanoate as a colorless oily substance (0.52 g, yield 15%).

$^1$H-NMR (300 MHz, CDCl$_3$) $\delta_H$ 0.81 and 0.92 (2×t, J=7.5 Hz, 3H, CH$_2$CH$_3$), 1.7-2.4 (m, 6H, PCH$_2$CH$_2$ and CH$_2$CH$_3$), 3.7-4.1 (m, 2H, NHCH$_2$CO), 4.5 (m, 1H, a-CH), 4.9 (m, H, POCHCO), 5.1-5.2 (m, 6H, 3×PhCH$_2$O), 5.5 (br m, 1H, NH), 5.6 and 5.8 (2×br m, 1H, NH), 7.1-7.4 (m, 20H, 4×Ph); $^{31}$P NMR (121 MHz, CDCl$_3$) $\delta_p$ 28.05 (24%), 28.31 (17%), 28.47 (25%), 28.66 (34%). Anal. calcd. for C$_{38}$H$_{41}$N$_2$O$_{10}$P: C, 63.68; H, 5.77; N, 3.91. found C, 63.66; H, 5.85; N, 3.86. HRMS (FAB, glycerol) calcd. for C$_{38}$H$_{42}$N$_2$O$_{10}$P (MH$^+$) 717.2577. found 717.2578.

Next, 0.25 g (0.35 mmol) of benzyl 2-(N-benzyloxycarbonylamino)-4-[1-[N-(benzyloxycarbonylmethyl)carbamoyl]propyl(phenyl)phosphono]butanoate was dissolved in 30 mL of a solvent mixture of methanol and water at 20:1 and mixed with 200 mg of 5% palladium-carbon and hydrogen gas was introduced for 45 minutes. The palladium-carbon was removed by Celite filtration and the filtrate was vacuum-concentrated. The residue was purified by medium pressure reversed-phase column chromatography ODS-S-50B. The column was eluted with a linear gradient of 30 to 60% methanol at a flow rate of 6 mL/min and the fractions containing the compound eluted at 60% methanol were collected. The elution and purity of the compound were confirmed by TLC (BuOH/AcOH/H$_2$O=5:2:2, ninhydrin coloration). After vacuum concentration, freeze drying was carried out to obtain 2-amino-4-[1-[N-(carboxymethyl)carbamoyl]propyl(phenyl)phosphono]butanoic acid (250 mg, yield 18%) as a colorless solid.

IR (KBr) $\nu_{max}$ 3600-2300 (br), 1668, 1652, 1593, 1541, 1489, 1455, 1398, 1348, 1205, 1051, 1007, 941, and 769 cm$^{-1}$; $^1$H NMR (300 MHz, D$_2$O) $\delta_H$ 0.84 (t, 3H, J=7.5 Hz, CH$_2$CH$_3$), 1.6-1.9 (m, 3H) and 2.2-2.4 (m, 3H) (PCH$_2$CH$_2$ and CH$_2$CH$_3$), 3.8-4.0 (m, 3H, a-CH and NHCH$_2$COOH), 4.9 (m, H, POCHCO), 7.26 (d, J=8.1 Hz, 2H), 7.33 (t, J=7.3 Hz, 1H) and 7.46 (t, J=7.8 Hz, 2H) (phenyl); $^{31}$P NMR (121 MHz, D$_2$O) $\delta_p$ 30.91. HRMS (FAB, glycerol) calcd for C$_{16}$H$_{24}$N$_2$O$_8$P (MH$^+$) 403.1270. found 403.1275.

Example 11

Synthesis of 2-amino-4-{[3-(carboxymethyl)phenyl](methyl)phosphono}butanoic Acid

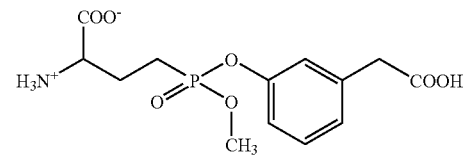

Benzyl 3-hydroxyphenylacetate 0.88 g (3.60 mmol) was added to 30 mL of a dry dichloromethane solution containing 3.60 mmol of benzyl 2-(N-benzyloxycarbonylamino)-4-[chloro(methyl)phosphono]butanoate obtained in the same manner as Example 1. After the solution was cooled to 0° C., 0.51 mL (3.60 mmol) of triethylamine was added and stirred at 0° C. for 15 minutes. Thereafter, the temperature was increased and reaction was carried out at 34° C. for 45 minutes. After the completion of the reaction was confirmed by TLC (EtOAc/hexane=1:1), the reaction mixture was vacuum-concentrated and the residue was dissolved in 30 mL of ethyl acetate and the insoluble salt was removed by filtration. The filtrate was vacuum-concentrated, and the crude product was purified by flash column chromatography on neutral silica gel 60 N using a solvent mixture of ethyl acetate and hexane at 4:3 to obtain benzyl 2-(N-benzyloxycarbonylamino)-4-{[3-(benzyloxycarbonylmethyl)phenyl](methyl)phosphono}butanoate as a colorless oily substance (0.72 g, yield 31%).

$^1$H-NMR (300 MHz, CDCl$_3$) $\delta_H$ 1.8-2.4 (m, 4H, PCH$_2$CH$_2$), 3.64 (s, 2H, CH$_2$COOBn), 3.71 (d, $^3$J$_{HP}$=10.8 Hz, 3H, POCH$_3$), 4.5 (m, 1H, a-CH), 5.10 and 5.12 (2×s, 4H, 2×OCH$_2$Ph), 5.17 (s, 2H, CHCOOCH$_2$Ph), 5.6 (br m, 1H, NH), 7.06-7.11 (m) and 7.22 (m) (4H, POC$_6$H$_4$), 7.3-7.5 (m, 15H, 3×Ph); $^{31}$P NMR (121 MHz, CDCl$_3$) $\delta_p$ 29.31. Anal. calcd. for C$_{35}$H$_{36}$NO$_9$P: C, 65.11; H, 5.62; N, 2.17. found: C, 65.36; H, 5.38; N, 2.11. HRMS (FAB, glycerol) calcd for C$_{35}$H$_{37}$NO$_9$P (MH$^+$) 646.2206. found 646.2233.

Next, 0.72 g (1.12 mmol) of benzyl 2-(N-benzyloxycarbonylamino)-4-{[3-(benzyloxycarbonylmethyl)phenyl](methyl)phosphono}butanoate was dissolved in 24 mL of a solvent mixture of methanol and water at 5:1 and mixed with 200 mg of 5% palladium-carbon, and hydrogen gas was introduced at room temperature for 2.5 hours. Thereafter, the palladium-carbon was removed by Celite filtration and the filtrate was vacuum-concentrated and the residue was freeze-dried from water to obtain 2-amino-4-{[3-(carboxymethyl)phenyl] (methyl)phosphono}butanoic acid (0.19 g, yield 51%) as a colorless solid.

$^{1}$H NMR (300 MHz, D$_2$O) $\delta_H$ 2.2-2.3 (m, 4H, PCH$_2$CH$_2$), 3.68 (s, 2H, PhCH$_2$COOH), 3.8-3.9 (m, 1H, a-CH), 3.86 (d, $^{3}J_{HP}$=11.1 Hz) and 3.87 (d, $^{3}J_{HP}$=11.1 Hz) (3H, POCH$_3$), 7.15 (s, 2H), 7.20 (d, J=7.8 Hz, 1H) and 7.41 (m, 1H) (phenyl); $^{31}$P NMR (121 MHz, D$_2$O) $\delta_p$ 32.52. Anal. calcd. for C$_{13}$H$_{18}$NO$_7$P.0.6H$_2$O: C, 45.65; H, 5.66; N, 4.09. found: C, 45.56; H, 5.43; N, 4.04. HRMS (FAB, glycerol) calcd for C$_{13}$H$_{19}$NO$_7$P (MH$^+$) 332.0899. found 332.0894.

Example 12

Synthesis of 2-amino-4-{[4-(carboxymethyl)phenyl](methyl)phosphono}butanoic Acid

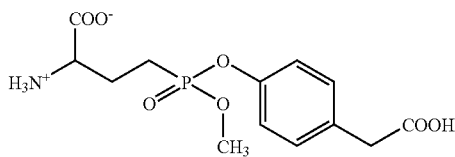

Benzyl 4-hydroxyphenylacetate 1.28 g (5.28 mmol) was added to 30 mL of a dry dichloromethane solution containing 4.82 mmol of benzyl 2-(N-benzyloxycarbonylamino)-4-[chloro(methyl)phosphono]butanoate obtained in the same manner as Example 1. After the solution was cooled to 0° C., 1.34 mL (9.45 mmol) of triethylamine was added and stirred at 0° C. for 15 minutes. Thereafter, the temperature was increased and reaction was carried out at 30° C. for 50 minutes. After the completion of the reaction was confirmed by TLC (EtOAc/hexane=8:5), the reaction solution was vacuum-concentrated and the residue was dissolved in 20 mL of ethyl acetate and the insoluble salt was removed by filtration. The filtrate was vacuum-concentrated and the crude product was purified by flash column chromatography on neutral silica gel 60 N using a solvent mixture of ethyl acetate and hexane at 8:5 to obtain a diastereomeric mixture of benzyl 2-(N-benzyloxycarbonylamino)-4-{[4-(benzyloxycarbonylmethyl)phenyl](methyl)phosphono}butanoate as a colorless oily substance (1.25 g, yield 40%).

$^{1}$H-NMR (300 MHz, CDCl$_3$) $\delta_H$ 1.8-2.4 (m, 4H, PCH$_2$CH$_2$), 3.62 (s, 2H, CH$_2$COOBn), 3.73 (d, $^{3}J_{HP}$=11.1 Hz, 3H, POCH$_3$), 4.5 (m, 1H, a-CH), 5.10 and 5.12 (2×s, 4H, 2×OCH$_2$Ph), 5.17 (s, 2H, CHCOOCH$_2$Ph), 5.5 (br m, 1H, NH), 7.10 (d, J=7.8 Hz) and 7.22 (d, J=8.4 Hz) (4H, POC$_6$H$_4$), 7.3-7.4 (m, 15H, 3×Ph); $^{31}$P NMR (121 MHz, CDCl$_3$) $\delta_p$ 29.36. Anal. calcd. for C$_{35}$H$_{36}$NO$_9$P: C, 65.11; H, 5.62; N, 2.17. found: C, 65.01; H, 5.71; N, 2.25. HRMS (FAB, glycerol) calcd for C$_{35}$H$_{37}$NO$_9$P (MH$^+$) 646.2206. found 646.2605.

Next, 1.25 g (1.94 mmol) of benzyl 2-(N-benzyloxycarbonylamino)-4-{[4-(benzyloxycarbonylmethyl)phenyl] (methyl)phosphono}butanoate was dissolved in 20 mL of acetic acid and mixed with 200 mg of 5% palladium-carbon and hydrogen gas was introduced at room temperature for 3.5 hours. Thereafter, the palladium-carbon was removed by Celite filtration and the filtrate was vacuum-concentrated and the residue was purified by medium pressure reversed-phase chromatography (ODS-S-50B). The column was eluted with a linear gradient of 30 to 60% methanol at a flow rate of 6 mL/min and the fractions of the compound eluted with 60% methanol were collected. The elution and purity of the compound were confirmed by TLC (BuOH/AcOH/H$_2$O=5:2:2, ninhydrin coloration). After vacuum concentration, freeze drying from water were carried out to obtain 2-amino-4-{[4-(carboxymethyl)phenyl](methyl)phosphono}butanoic acid (0.41 g, yield 64%) as a colorless solid.

$^{1}$H NMR (300 MHz, D$_2$O) $\delta_H$ 2.2-2.3 (m, 4H, PCH$_2$CH$_2$), 3.67 (s, 2H, PhCH$_2$COOH), 3.8-4.0 (m, 1H, a-CH), 3.88 (d, $^{3}J_{HP}$=11.4 Hz, 3H, POCH$_3$), 7.21 (d, J=8.1 Hz, 2H) and 7.35 (d, J=8.4 Hz, 2H) (phenyl); $^{31}$P NMR (121 MHz, D$_2$O) $\delta_p$ 32.56. Anal. calcd. for C$_{13}$H$_{18}$NO$_7$P.1.0H$_2$O: C, 44.70; H, 5.77; N, 4.01. found: C, 44.42; H, 5.43; N, 3.83. HRMS (FAB, glycerol) calcd for C$_{13}$H$_{19}$NO$_7$P (MH$^+$) 332.0899. found 332.0900.

Example 13

Synthesis of 2-amino-4-[4-carboxyphenyl(methyl)phosphono]butanoic Acid

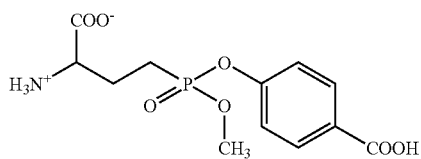

1.10 g (4.82 mmol) of commercially available benzyl 4-hydroxybenzoate was added to 30 mL of a dry dichloromethane solution containing 4.82 mmol of phosphonic acid dichloride obtained in the same manner as Example 1 and cooled to −65° C. Triethylamine 0.74 mL (5.31 mmol) was added, and the mixture was stirred at −65° C. for 10 minutes. Thereafter, the cooling bath was removed and the temperature was slowly increased to room temperature, and reaction was carried out further at 30° C. for 30 minutes to obtain the corresponding phosphonic acid monochloride. The resulting reaction solution was further mixed with 0.17 g (5.31 mmol) of methanol and 1.34 mL (9.64 mmol) of triethylamine at 0° C. and reaction was carried out for 10 minutes in that state and further at a temperature increased to 30° C. for another 1 hour. After the completion of the reaction was confirmed by TLC (EtOAc/hexane=4:3), the reaction solution was vacuum-concentrated, and the residue was dissolved in 20 mL of ethyl acetate and the insoluble salt was removed by filtration. The filtrate was vacuum-concentrated and the crude product was purified by flash column chromatography on neutral silica gel 60 N using a solvent mixture of ethyl acetate and hexane at 4:3 ratio to obtain a diastereomeric mixture of benzyl 2-(N-benzyloxycarbonylamino)-4-[4-(benzyloxycarbonyl)phenyl(methyl)phosphono]butanoate as a colorless oily substance (1.46 g, yield 48%).

$^{1}$H-NMR (300 MHz, CDCl$_3$) $\delta_H$ 1.7-2.4 (m, 4H, PCH$_2$CH$_2$), 3.74 (d, $^{3}J_{HP}$=11.1 Hz, 3H, POCH$_3$), 4.5 (m, 1H, a-CH), 5.10 and 5.17 (2×s, 4H, CHCOOCH$_2$Ph and NHCOOCH$_2$Ph), 5.35 (s, 2H, COOCH$_2$Ph), 5.47 (br d, J=7.2 Hz, 1H, NH), 7.2 (d, J=8.4 Hz, 2H) and 8.0 (d, J=9.0 Hz, 2H) (POC$_6$H$_4$), 7.3-7.5 (m, 15H, 3×Ph); $^{31}$P NMR (121 MHz, CDCl$_3$) δ$_p$ 29.55. Anal. calcd. for C$_{34}$H$_{34}$NO$_9$P: C, 64.65; H, 5.43; N, 2.22. found: C, 64.72; H, 5.54; N, 2.22. HRMS (FAB, glycerol) calcd for C$_{35}$H$_{35}$NO$_9$P (MH$^+$) 632.2050. found 632.2026.

Next, 1.40 g (2.22 mmol) of benzyl 2-(N-benzyloxycarbonylamino)-4-[4-(benzyloxycarbonyl)phenyl(methyl)phosphono]butanoate was dissolved in 28 mL of a solvent mixture of acetic acid and water at 2:1 and mixed with 200 mg of 5% palladium-carbon and hydrogen gas was introduced at room temperature for 2.2 hours. Thereafter, the palladium-carbon was removed by Celite filtration and the filtrate was vacuum-concentrated, and the residue was freeze-dried from water to obtain 2-amino-4-[4-carboxyphenyl(methyl)phosphono]butanoic acid (0.62 g, yield 89%) as a colorless solid.

$^1$H NMR (300 MHz, D$_2$O) δ$_H$ 2.2-2.3 (m, 4H, PCH$_2$CH$_2$), 3.8-3.9 (m, 1H, a-CH), 3.89 (d, $^3$J$_{HP}$=11.4 Hz, 3H, POCH$_3$), 7.32 (d, J=7.8 Hz, 2H) and 8.05 (d, J=8.4 Hz, 2H) (phenyl); $^{31}$P NMR (121 MHz, D$_2$O) δ$_p$ 32.40. Anal. calcd. for C$_{12}$H$_{16}$NO$_7$P.0.6H$_2$O: C, 43.94; H, 5.28; N, 4.27. found: C, 44.19; H, 5.14; N, 3.94. HRMS (FAB, glycerol) calcd for C$_{12}$H$_{17}$NO$_7$P (MH$^+$) 318.0743. found 318.0747.

Example 14

Synthesis of 2-amino-4-[methyl(3-nitrophenyl)phosphono]butanoic Acid

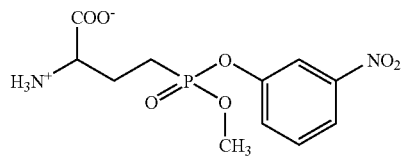

3-Nitrophenol 0.68 (4.91 mmol) was added to 20 mL of a dry dichloromethane solution containing 4.91 mmol of benzyl 2-(N-benzyloxycarbonylamino)-4-[chloro(methyl)phosphono]butanoate obtained in the same manner as Example 1 and cooled to −20° C. and thereafter, 0.50 g (4.91 mmol) of triethylamine was added and stirred for 15 minutes. Thereafter, the temperature was increased to room temperature and reaction was carried out overnight. After the completion of the reaction was confirmed by TLC (EtOAc/hexane=1:1), the reaction mixture was vacuum-concentrated and the residue was dissolved in 20 mL of acetone and the insoluble salt was removed by filtration. The filtrate was vacuum-concentrated and the crude product was purified by flash column chromatography on neutral silica gel 60 N using a solvent mixture of ethyl acetate and hexane at 1:1 ratio to obtain a diastereomeric mixture of benzyl 2-(N-benzyloxycarbonylamino)-4-[methyl(3-nitrophenyl)phosphono]butanoate as a colorless oily substance (1.18 g, yield 44%).

$^1$H-NMR (300 MHz, CDCl$_3$) δ$_H$ 1.8-2.3 (m, 4H, PCH$_2$CH$_2$), 3.77 (d, $^3$J$_{HP}$=11.4 Hz, 3H, POCH$_3$), 4.5 (m, 1H, a-CH), 5.11 (s, 2H, NHCOOCH$_2$Ph), 5.19 (s, 2H, CHCOOCH$_2$Ph), 5.5 (d, J=7.8 Hz, 1H, NH), 7.3-7.4 (m, 10H, 2×Ph), 7.5-7.6 (m, 2H) and 8.0-8.1 (m, 2H) (3-nitrophenyl); $^{31}$P NMR (121 MHz, CDCl$_3$) δ$_p$ 30.44. Anal. calcd. for C$_{26}$H$_{27}$N$_2$O$_9$P: C, 57.57; H, 5.02; N, 5.16. found: C, 57.48; H, 5.05; N, 5.03. HRMS (FAB, glycerol) calcd for C$_{26}$H$_{28}$N$_2$O$_9$P (MH$^+$) 543.1532. found 543.1523.

Next, 1.09 g (2.01 mmol) of benzyl 2-(N-benzyloxycarbonylamino)-4-[methyl(3-nitrophenyl)phosphono]butanoate and 1.30 g (12.0 mmol) of anisole were dissolved in 10 mL of dry nitromethane and mixed with 0.80 g (6.00 mmol) of aluminum trichloride and reaction was carried out at room temperature for 3 hours. Thereafter, 20 mL of water was added and stirred for 10 minutes. The mixture was washed with 50 mL of ether three times and the water layer was removed, and methanol was added to adjust the final concentration of methanol to be 30%. The solution was passed through a short column of neutral silica gel 60N to remove aluminum hydroxide. Without being concentrated, 30 mL of the effluent was purified by medium pressure reversed-phase column chromatography ODS-S-50B. The column was eluted with a linear gradient of 30 to 60% methanol at a flow rate of 6 mL/min and the fractions containing the compound eluted at 60% methanol were collected. The elution and purity of the compound were confirmed by TLC (BuOH/AcOH/H$_2$O=5:2:2, ninhydrin coloration). After vacuum concentration, freeze drying was carried out from water to obtain 2-amino-4-[methyl(3-nitrophenyl)phosphono]butanoic acid (0.40 g, yield 63%) as a colorless solid.

$^1$H NMR (300 MHz, D$_2$O) δ$_H$ 2.1-2.4 (m, 4H, PCH$_2$CH$_2$), 3.8-3.9 (m, 1H, a-CH), 3.88 (d, $^3$J$_{HP}$=12.0 Hz, 3H, POCH$_3$), 7.62 (m, 2H), 8.04 (s, 1H) and 8.13 (m, 1H) (3-nitrophenyl); $^{31}$P NMR (121 MHz, D$_2$O) δ$_p$ 32.93. Anal. calcd. for C$_{11}$H$_{15}$N$_2$O$_7$P.0.5H$_2$O: C, 40.37; H, 4.93; N, 8.56. found: C, 40.56; H, 4.95; N, 8.68. HRMS (FAB, glycerol) calcd for C$_{11}$H$_{16}$N$_2$O$_7$P (MH$^+$) 319.0695. found 319.0694.

Example 15

Synthesis of 2-amino-4-[3-carboxyphenyl(methyl)phosphono]butanoic Acid

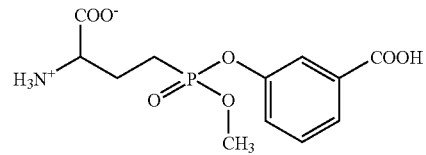

Benzyl 3-hydroxybenzoate 1.21 g (5.30 mmol) was added to 40 mL of a dry dichloromethane solution containing 4.82 mmol of benzyl 2-(N-benzyloxycarbonylamino)-4-[chloro(methyl)phosphono]butanoate obtained in the same manner as Example 1. After cooled to 0° C., 0.81 mL (5.78 mmol) of triethylamine was added and stirred at 0° C. for 15 minutes and thereafter, the temperature was increased to room temperature and reaction was carried out further at 30° C. for 1.5 hours. After the completion of the reaction was confirmed by TLC (EtOAc/hexane=8:5), the reaction mixture was vacuum-concentrated, and the residue was dissolved in 30 mL of acetone and the insoluble salt was removed by filtration. The filtrate was vacuum-concentrated and the crude product was purified by flash column chromatography on neutral silica gel 60 N using a solvent mixture of ethyl acetate and hexane at 8:5 ratio to obtain a diastereomeric mixture of benzyl 2-(N-benzyloxycarbonylamino)-4-{[3-(benzyloxycarbonyl)phenyl](methyl)phosphono} butanoate as a colorless oily substance (1.49 g, yield 49%).

$^1$H-NMR (300 MHz, CDCl$_3$) δ$_H$ 1.8-2.4 (m, 4H, PCH$_2$CH$_2$), 4.5 (m, 1H, a-CH), 5.10 (s, 2H, NHCOOCH$_2$Ph), 5.17 (s, 2H, CHCOOCH$_2$Ph), 5.36 (s, 2H, COOCH$_2$Ph), 5.5

(d, J=6.9 Hz, 1H, NH), 7.3-7.9 (m, 19H, 4×Ph); $^{31}$P NMR (121 MHz, CDCl$_3$) $\delta_p$ 29.75. Anal. calcd. for C$_{34}$H$_{34}$NO$_9$P: C, 64.65; H, 5.43; N, 2.22. found: C 64.26; H, 5.50; N, 2.28. HRMS (FAB, glycerol) calcd for C$_{34}$H$_{35}$NO$_9$P (MH$^+$) 632.2050. found 632.2056.

Next, 1.31 g (2.07 mmol) of benzyl 2-(N-benzyloxycarbonylamino)-4-{[3-(benzyloxycarbonyl)phenyl](methyl)phosphono} butanoate was dissolved in 28 mL of a solvent mixture of acetic acid and water at 3:1 and mixed with 200 mg of 5% palladium-carbon and hydrogen gas was introduced at room temperature for 3 hours. Thereafter, the palladium-carbon was removed by Celite filtration and the filtrate was vacuum-concentrated and the residue was freeze-dried from water to obtain 2-amino-4-[3-carboxyphenyl(methyl)phosphono]butanoic acid (0.59 g, yield 90%) as a colorless solid.

$^1$H NMR (300 MHz, D$_2$O) $\delta_H$ 2.0-2.4 (m, 4H, PCH$_2$CH$_2$), 3.8-3.9 (m, 1H, a-CH), 3.88 (d, $^3J_{HP}$=11.1 Hz, 3H, POCH$_3$), 7.46 (d, J=8.1 Hz, 1H), 7.55 (t, J=8.1 Hz, 1H), 7.77 (s, 1H) and 7.89 (d, J=7.8 Hz, 1H) (phenyl); $^{31}$P NMR (121 MHz, D$_2$O) $\delta_p$ 32.63. Anal. calcd. for C$_{12}$H$_{16}$NO$_7$P.0.6H$_2$O: C, 43.94; H, 5.28; N, 4.27. found: C, 43.74; H, 5.11; N, 4.25. HRMS (FAB, glycerol) calcd for C$_{12}$H$_{17}$NO$_7$P (MH$^+$) 318.0743. found 318.0755.

Example 16

Synthesis of 2-amino-4-{[3-(2-carboxyethyl)phenyl](methyl)phosphono}butanoic Acid

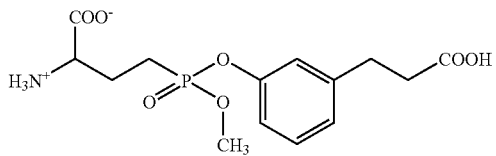

Benzyl 3-(3-hydroxyphenyl)propanoate 1.75 g (6.83 mmol) was added to 30 mL of a dry dichloromethane solution containing 4.82 mmol of benzyl 2-(N-benzyloxycarbonylamino)-4-[chloro(methyl)phosphono]butanoate obtained in the same manner as Example 1. After cooled to 0° C., 1.34 mL (9.64 mmol) of triethylamine was added and stirred at 0° C. for 15 minutes, and thereafter, the reaction was carried out further at room temperature overnight. After the completion of the reaction was confirmed by TLC (EtOAc/hexane=4:3), the reaction mixture was vacuum-concentrated and the residue was dissolved in 30 mL of acetone and the insoluble salt was removed by filtration. The filtrate was vacuum-concentrated and the crude product was purified by flash column chromatography on neutral silica gel 60 N using a solvent mixture of ethyl acetate and hexane at 7:5 ratio to obtain a diastereomeric mixture of benzyl 2-(N-benzyloxycarbonylamino)-4-{[3-(2-benzyloxycarbonylethyl)phenyl] (methyl)phosphono}butanoate as a colorless oily substance (0.82 g, yield 26%).

$^1$H-NMR (300 MHz, CDCl$_3$) $\delta_H$ 1.8-2.4 (m, 4H, PCH$_2$CH$_2$), 2.66 (t, J=7.8 Hz, 2H, CH$_2$CH$_2$COO), 2.94 (t, J=7.8 Hz, 2H, CH$_2$CH$_2$COO), 3.72 (d, $^3J_{HP}$=11.1 Hz, 3H, POCH$_3$), 4.5 (m, 1H, a-CH), 5.10 (s, 4H, COOCH$_2$Ph and NHCOOCH$_2$Ph), 5.17 (s, 2H, CHCOOCH$_2$Ph), 5.5 (br d, J=7.5 Hz, 1H, NH), 7.0-7.4 (m, 19H, 3×Ph and C$_6$H$_4$); $^{31}$P NMR (121 MHz, CDCl$_3$) $\delta_p$ 29.21. Anal. calcd. for C$_{36}$H$_{38}$NO$_9$P: C, 65.55; H, 5.81; N, 2.12. found: C, 65.36; H, 5.88; N, 2.28. HRMS (FAB, glycerol) calcd for C$_{36}$H$_{39}$NO$_9$P (MH$^+$) 660.2363. found 660.2359.

Next, 0.68 g (1.03 mmol) of benzyl 2-(N-benzyloxycarbonylamino)-4-{[3-(2-benzyloxycarbonylethyl)phenyl](methyl)phosphono}butanoate was dissolved in 50 mL of a solvent mixture of methanol and water at 4:1 and mixed with 240 mg of 5% palladium-carbon, and hydrogen gas was introduced at room temperature for 5 hours. Thereafter, the palladium-carbon was removed by Celite filtration and the filtrate was vacuum-concentrated and the residue was freeze-dried from water to obtain 2-amino-4-{[3-(2-carboxyethyl)phenyl](methyl)phosphono}butanoic acid (0.31 g, yield 86%) as a colorless solid.

$^1$H NMR (300 MHz, D$_2$O) $\delta_H$ 2.0-2.2 (m, 4H, PCH$_2$CH$_2$), 2.68 (t, J=7.2 Hz, 2H, PhCH$_2$CH$_2$COO), 2.93 (t, J=7.2 Hz, 2H, PhCH$_2$CH$_2$COO), 3.8-3.9 (m, 1H, a-CH), 3.84 (d, $^3J_{HP}$=11.4 Hz, 3H, POCH$_3$), 7.07 (d, J=9.3 Hz, 2H), 7.17 (d, J=7.2 Hz, 1H) and 7.36 (t, J=7.8 Hz, 1H) (phenyl); $^{31}$P NMR (121 MHz, D$_2$O) $\delta_p$ 32.48. Anal. calcd. for C$_{14}$H$_{20}$NO$_7$P.0.6H$_2$O: C, 47.22; H, 6.00; N, 3.93. found: C, 47.32; H, 5.88; N, 3.99. HRMS (FAB, glycerol) calcd for C$_{14}$H$_{21}$NO$_7$P (MH$^+$) 346.1056. found 346.1059.

Example 17

Synthesis of 2-amino-4-(diphenylphosphono)butanoic Acid

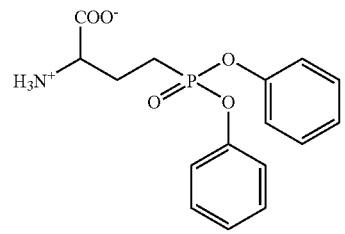

At the time of synthesizing benzyl 2-(N-4-nitrobenzyloxycarbonylamino)-4-[methyl(phenyl)phosphono]butanoate in Example 3, 0.64 g of benzyl 2-(N-4-nitrobenzyloxycarbonylamino)-4-(diphenylphosphono)butanoate was obtained as a byproduct.

$^1$H-NMR (300 MHz, CDCl$_3$) $\delta_H$ 2.0-2.4 (m, 4H, PCH$_2$CH$_2$), 4.51 (m, 1H, a-CH), 5.21 (m, 4H, 2×OCH$_2$Ph), 5.7 (br d, J=7.5 Hz, 1H, NH), 7.1-7.4 (m, 15H, 3×Ph), 7.5 (d, J=8.7 Hz, 2H) and 8.2 (d, J=8.7 Hz, 2H) (4-nitrophenyl); $^{31}$P NMR (121 MHz, CDCl$_3$) $\delta_p$ 24.40. Anal. calcd. for C$_{31}$H$_{29}$N$_2$O$_9$P: C, 61.59; H, 4.84; N, 4.63. found: C, 61.94; H, 4.97; N, 4.49.

Next, 0.64 g (1.06 mmol) of benzyl 2-(N-4-nitrobenzyloxycarbonylamino)-4-(diphenylphosphono)butanoate was dissolved in 20 mL of acetic acid and mixed with 86 mg of 10% palladium-carbon and hydrogen gas was introduced at room temperature for 2 hours. Thereafter, the palladium-carbon was removed by Celite filtration and the filtrate was vacuum-concentrated, and the residue was crystallized from a solvent mixture of acetonitrile and water to obtain 2-amino-4-(diphenylphosphono)butanoic acid (0.13 g, yield 37%) as a colorless solid.

$^1$H-NMR (300 MHz, D$_2$O) $\delta_H$ 2.3-2.5 (m, 4H, PCH$_2$CH$_2$), 3.87 (t, J=4.8 Hz, 1H, a-CH), 7.19 (d, J=7.8 Hz, 4H), 7.31 (t, J=7.8 Hz, 2H) and 7.44 (t, J=8.4 Hz, 4H) (phenyl); $^{31}$P NMR (121 MHz, D$_2$O) $\delta_p$ 28.20. Anal. calcd. for $C_{16}H_{18}NO_5P\cdot H_2O$: C, 54.39; H, 5.71; N, 3.96. found: C, 54.40; H, 5.51; N, 4.25. HRMS (FAB, glycerol) calcd for $C_{16}H_{19}NO_5P$ (MH$^+$) 336.1001. found 336.1001.

[Experiment of Inhibitory Activity to GGT]

Purified enzyme of *E-coli* GGT and crude enzyme of human GGT were employed as GGT samples for an inhibition experiment. The enzyme whose physicochemical properties are described in the Document (Hideyuki Suzuki, Hidehiko Kumagai, Tatsurokukro Tochikura "gamma-Glutamyltranspeptidase from *Escherichia coli* K-12: Purification and Properties" Journal of Bacteriology, December 1986, Vol. 168, No. 3, p. 1325-1331) was used as a purified enzyme of *E-coli* GGT. Enzyme [HC-GTP (product number), 603AA (lot number)] manufactured by Asahi Kasei Co., Ltd. was used as a crude enzyme of human GGT. The crude enzyme of human GGT contained a large amount of bovine serum albumin (BSA) to stabilize the enzyme, and the GGT concentration was 1% or lower.

In the experiment, at first, Michaelis constants ($K_m$) for 7-(γ-L-glutamylamino)-4-methylcoumarin as substrate were measured by a fluorescence method [Smith, G. D.; Ding, J. L.; Peters, T. J. Anal. Biochem. 100, 136-139 (1979)] for the hydrolytic activities of *E-coli* GGT and human GGT.

In the hydrolytic assay of *E. coli* GGT, 10 μL of a 0.42 nM enzyme solution was added to a 100 mM succinic acid-sodium hydroxide buffer solution (pH 5.5) in a total volume of 1 mL containing 100 μL of 2 μM substrate aqueous solution. The product, 7-amino-4-methylcoumarin (AMC), released along with the enzyme reaction was traced continuously at 25° C. using a fluorospectrophotometer F-2000 manufactured by Hitachi Ltd. (excitation wavelength: 350 nm, emission wavelength: 440 nm). The AMC concentration was separately measured by forming a calibration curve showing the relation of the fluorescence intensity (F) and the concentration (C) using standard solutions and was calculated from the relational expression (1) of the fluorescence intensity alteration (ΔF) and concentration alteration (ΔC).

[Expression 1]

$$\Delta F/\Delta C=0.11 \text{ nM}^{-1} \quad (1)$$

The fluorescence intensity was proportional to the AMC concentration up to 2.0 μM. As a result, $K_m$ value for 7-(γ-L-glutamylamino)-4-methylcoumarin was 0.2 μM under this condition.

In the hydrolytic assay of human GGT, the measurement was carried out in the same manner as that in the hydrolytic assay of *E-coli* GGT, except that the substrate concentration was changed to 4.0 μM and therefore, the explanation of the common portions was omitted. As a result of the measurement, $K_m$ value for 7-(γ-L-glutamylamino)-4-methylcoumarin was 12.6 μM.

The protein concentration was measured using a pigment for quantitative determination of proteins produced by Bio-Rad Laboratories Inc. on the basis of BSA as a standard protein.

Next, a second-order rate constant for enzyme inactivation $k_{on}$ was measured by either a continuous assay or a discontinuous assay. Both of the continuous and discontinuous assay for measuring inhibitory activity to GGT were carried out under a pseudo-first-order reaction condition.

In the continuous assay, while the temperature was kept at 25° C., the 100 mM succinic acid-sodium hydroxide buffer solutions (pH 5.5) containing an inhibitor in various concentrations and the substrate were preincubated for equilibrium. Herein, 0.2 μM of the substrate was used for the case of *E-coli* GGT and 0.4 μM of the substrate was used for the case of human GGT. Thereafter, the enzyme solution of the *E-coli* GGT was added in a manner that the final concentration became 0.04 nM and also the human GGT crude enzyme solution was added in a manner that the final concentration became 5 μg/mL. Accordingly, the reaction was started and the release of AMC (increase of the fluorescence intensity) was continuously traced for 10 minutes. The obtained fluorescence intensity was plotted against the time as shown in FIG. 1 and FIG. 2.

Figure 2:
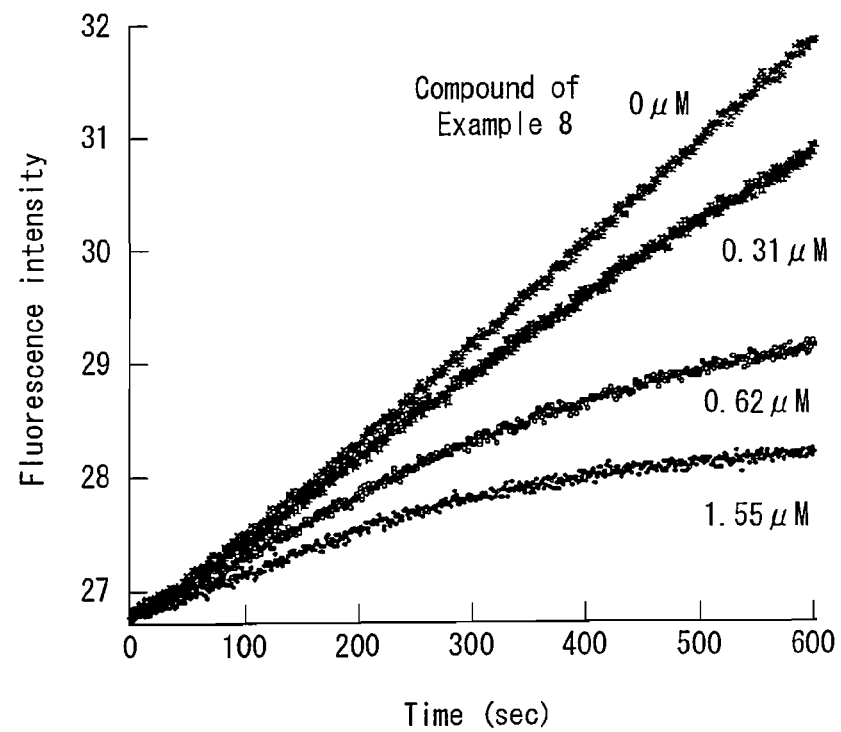
FIG. 2 is a graph showing fluorescence intensity of AMC in relation to the concentration of the compound of Example 8 and the reaction time in the case of causing reaction of the compound and human GGT.

FIG. 1 shows the fluorescence intensity of AMC released from substrate in the case of reaction of the compound of Example 8, as one example of the inhibitors, with *E-coli* GGT and FIG. 2 shows the fluorescence intensity of AMC released from substrate in the case of reaction of the compound of Example 8, as one example of the inhibitors, with human GGT. The fluorescence intensity was plotted in the vertical axis and the time was plotted in the horizontal axis of FIGS. 1 and 2.

As shown in FIGS. 1 and 2, the inclination of the inhibition curves become small with the lapse of time, and the curvatures of the respective inhibition curves differ in accordance with the inhibitor concentrations. The fluorescence intensity data obtained from the respective curves was applied to the following pseudo-first-order rate equation (2) and the observed pseudo-first-order rate constant for enzyme inactivation ($k_{obs}$) was calculated by nonlinear regression analysis [Stein, R. L. et al. Biochemistry 26, 2682-2689 (1987)].

[Equation 2]

$$[P]=[P]_\infty[1-\exp(-k_{obs}t)] \quad (2)$$

Herein, [P] and [P]$_\infty$ denote the product concentration at a time (t) and an infinite time (t=∞).

When the $k_{obs}$ was plotted against to the inhibitor concentration ([I]), a linear relation was obtained until the maximum extent of the experimentally possible inhibitor concentration. Therefore, the second-order rate constant for enzyme inactivation $k_{on}$ was calculated using the following equation (3) deduced from the kinetic mechanism.

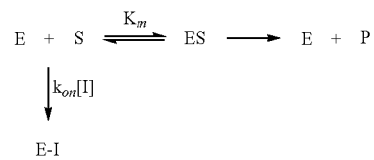

[Equation 3]

$$k_{obs}=k_{on}[I]/(1+[S]/K_m) \quad (3)$$

Herein, S denotes 7-(γ-L-glutamylamino)-4-methylcoumarin. The substrate concentration [S] for *E-coli* GGT is 0.2 μM and the $K_m$ value is 0.2 μM. The substrate concentration [S] for human GGT is 4.0 μM and the $K_m$ value is 12.6 μM. The kinetic data was obtained by nonlinear regression analysis using Kaleida graph, a program produced by Synergy Software.

Further, in the discontinuous assay, an inhibitor in various concentrations was dissolved in 100 mM succinic acid-sodium hydroxide buffer solution (pH 5.5) and the enzyme solution was added to the resulting buffer solutions. Herein, in the case of *E-coli* GGT, the enzyme solution was added in a manner that the final concentration became 0.4 nM and also the human GGT crude enzyme solution was added in a manner that the final concentration became 0.5 mg/mL. Accordingly, the reaction of the inhibitor and each GGT was conducted at 25° C. An aliquot (10 μL) of each of the reaction solutions were sampled at every specified time to measure the remaining enzyme activity by the above-mentioned enzyme activation method. The remaining enzyme activity at every time was analyzed by nonlinear regression using the pseudo-first-order rate equation (4) of enzyme inactivation to calculate the value of $k_{obs}$.
[Equation 4]

$$a_t/a_0 = \exp(-k_{obs}t) \quad (4)$$

Herein, at denotes the remaining activity at time (t) and $a_0$ denotes the enzyme activity before inhibition (t=0). The nonlinear regression analysis was carried out using Kaleida graph.

The $k_{obs}$ was plotted against the inhibitor concentrations ([I]) and the linear relation was obtained until the maximum extent of the experimentally possible inhibitor concentration. Accordingly $k_{on}$ was calculated from the $k_{obs}$ value according to the following equation (5).
[Equation 5]

$$k_{obs} = k_{on}[I] \quad (5)$$

[The results of experiment of inhibitory activities to GGT]

Table 2 shows the results of the second-order rate constant for GGT inactivation $k_{on}$ of each of the compounds of Examples 1 to 17 and Comparative Example 1 measured by the above tests. Herein, acivicin ((aS, 5S)-acivicin) was used for Comparative Example 1.

TABLE 2

|  | | $k_{on}$ (M$^{-1}$S$^{-1}$) | |
| --- | --- | --- | --- |
|  | p$K_a$ | E-coli GGT | Human GGT |
| Example 1 | 10.26 | 23 | 0.24 |
| Example 2 | 10.10 | 19.5 | 0.16 |
| Example 3 | 9.98 | 115 | 0.40 |
| Example 4 | 9.41 | 607 | 5.0 |
| Example 5 | 8.51 | 2800 | 11.5 |
| Example 6 | 7.95 | 12000 | 45.9 |
| Example 7 | 7.15 | 35000 | 125.1 |
| Example 8 | 8.2 | 15700 | 2400 |
| Example 9 | 9.98 | 9.0 | 0.023 |
| Example 10 | 9.98 | 80.9 | 74.5 |
| Example 11 | 9.71 | 150 | 51 |
| Example 12 | 9.84 | 200 | 0.33 |
| Example 13 | 8.70 | 3200 | 5.2 |
| Example 14 | 8.36 | 5100 | 49 |
| Example 15 | 9.14 | 450 | 1.63 |
| Example 16 | 10.06 | 71 | 7.67 |
| Example 17 | 9.98 | 28 | 0.41 |
| Comparative Example 1 | −6.18 | 4210 ± 10 | 0.40 ± 0.02 |

From the results shown in Table 2, all of the compounds of Examples 1 to 17 have the inhibitory effect on E. coli and human GGT. Particularly, since the compounds of Examples 6 to 8 and 14 have higher second-order rate constants for enzyme inactivation $k_{on}$ toward E. coli GGT than the second-order rate constant for enzyme inactivation $k_{on}$ of acivicin of Comparative Example 1, the inactivation rates of E. coli GGT by these compounds are higher than the inactivation rate by acivicin. Accordingly, the inhibitory effect of the compounds of Examples 6 to 8 and 14 on E. coli GGT is better than the inhibitory effect of acivicin on E. coli GGT.

Further, since the compounds of Examples 4 to 8, 10, 11, and 13 to 16 have higher the second-order rate constant for enzyme inactivation $k_{on}$ toward the human GGT than the second-order rate constant for enzyme inactivation $k_{on}$ of acivicin of Comparative Example 1, the inactivation rates of human GGT by these compounds are higher than the inactivation rate by acivicin. Accordingly, the inhibitory effect of the compounds of Examples 4 to 8, 10, 11, and 13 to 16 on human GGT is better than the inhibitory effect of acivicin on human GGT.

[Relation of Stability and Inhibitory Activity on GGT of Compound]

Figure 3:
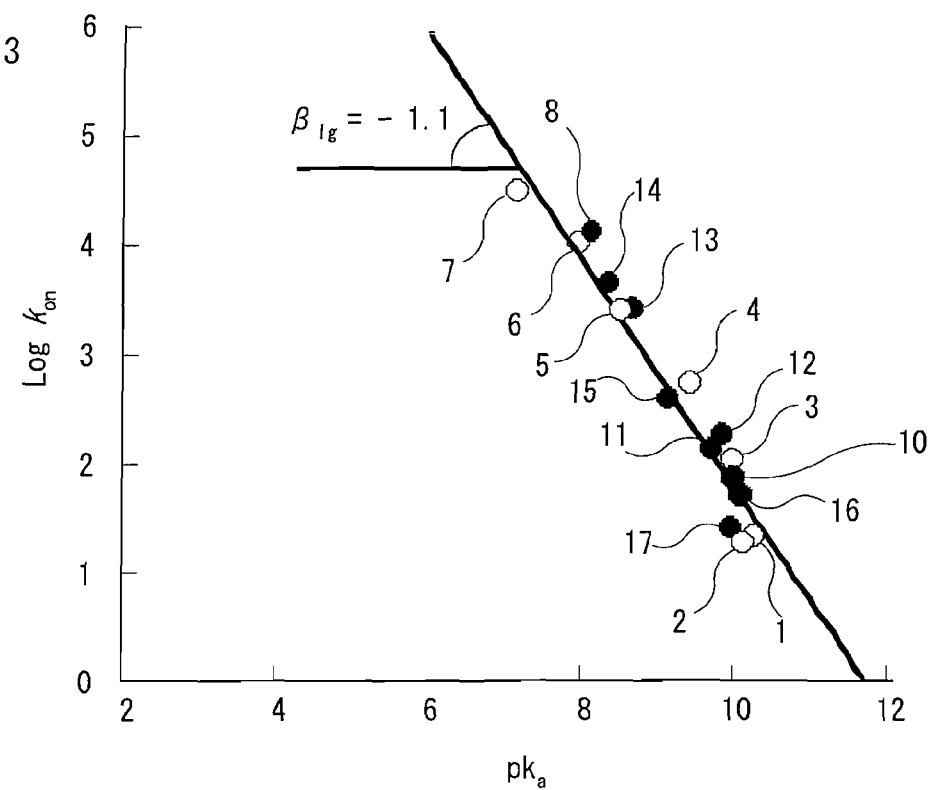
FIG. 3 is a graph showing the relation of dissociation constant $K_a$ of an aryl group of the respective compounds and the second-order rate constant $k_{on}$ of *E-coli* GGT enzyme inactivation for compounds of Examples 1 to 17.

FIG. 3 shows the relation of the dissociation constant $K_a$ of an aryl group in each compound and the second-order rate constant $k_{on}$ of E-coli GGT inactivation with respect to the compounds of Examples 1 to 8 and 10 to 17. In FIG. 3, log $k_{on}$ of the compounds is plotted in the vertical axis and p$K_a$ of an aryl group of each compound is plotted in the horizontal axis.

From the results shown in FIG. 3, the plots of the compounds of Examples 1 to 8 and 10 to 17 become linear and the log $k_{on}$ of these compounds and p$K_a$ of an aryl group are proportional. In general, when p$K_a$ of an aryl group of a compound is lower, the aryl group tends to be dissociated more easily and the chemical reactivity of the compound itself becomes higher. Therefore, from the results of FIG. 3, it can be understood that the compounds of Examples 1 to 8 and 10 to 17 react with E-coli GGT according to their chemical reactivity.

Figure 4:
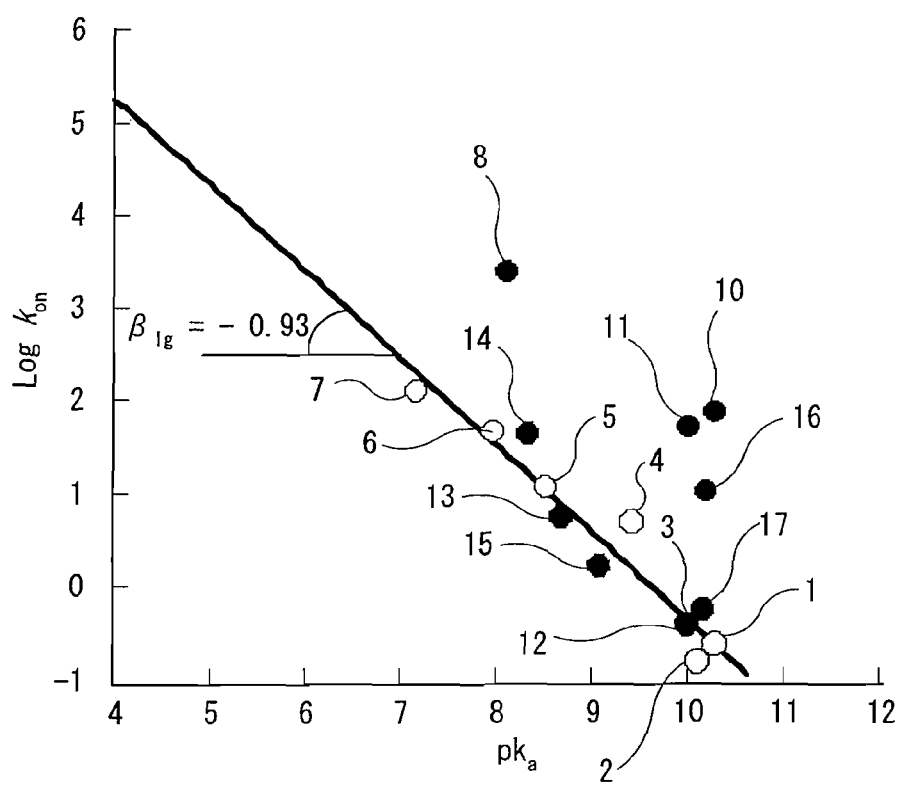
FIG. 4 is a graph showing the relation of dissociation constant $K_a$ of an aryl group of the respective compounds and the second-order rate constant $k_{on}$ of human GGT enzyme inactivation for compounds of Examples 1 to 17.

Further, with respect to the compounds of Examples 1 to 8 and 10 to 17, FIG. 4 shows the relation of the dissociation constant $K_a$ of an aryl group in each compound and the second-order rate constant $k_{on}$ of human GGT inactivation. In FIG. 4, log $k_{on}$ of the compounds is plotted in the vertical axis and p$K_a$ of an aryl group of each compound is plotted in the horizontal axis.

From the results shown in FIG. 4, the plots of the compounds of Examples 1 to 7, 12 to 15, and 17 become linear and the log $k_{on}$ of these compounds and p$K_a$ of an aryl group are proportional. On the other hand, the plots of the compounds of Examples 8, 10, 11, and 16 deviate upward from the above straight line and log $k_{on}$ of the compounds of Examples 8, 10, 11, and 16 show a higher value than the log $k_{on}$ on the straight line. Therefore, the inhibitory effect of the compounds of Examples 8, 10, 11, and 16 on human GGT is higher than that estimated from the dissociation ability estimated from p$K_a$ value of an aryl group, that is, chemical reactivity of these compounds themselves and thus is relatively high as compared with that of compounds of Examples 1 to 7, 12 to 15, and 17.

Further, the compounds of Examples 8, 10, 11, and 16 show higher inhibitory effect than expected from the chemical reactivity of the compounds themselves on human GGT as described above and on the other hand, as shown in FIG. 3, show inhibitory effect approximately same as expected from the chemical reactivity of the compounds themselves on E-coli GGT. Therefore, it can be understood that the compounds of Examples 8, 10, 11, and 16 have a special characteristic of particularly higher inhibitory effect on human GGT than on E-coli GGT.

In particular, with respect to compounds of Examples 11 and 12, in one hand, the carboxymethyl is substituted at the meta-position of the phenyl group in the compound of Example 11, and on the other hand, the carboxymethyl is substituted at the para-position of the phenyl group in the compound of Example 12, and their molecular structures are analogous except that the difference in the bonding position of the carboxymethyl group. Further, p$K_a$ value of an aryl group and the second-order rate constant $k_{on}$ for E. coli GGT inactivation are almost the same respectively between the compounds of Examples 11 and 12. That is the compounds of Examples 11 and 12 show approximately the same chemical reactivity and inhibitory activity to E. coli GGT. However, the compound of Example 11 has $k_{on}$: 51 (M$^{-1}$ s$^{-1}$) of human GGT enzyme inactivation, about 155 times as high as the second-order rate constant $k_{on}$: 0.33 (M$^{-1}$ s$^{-1}$) of human GGT inactivation of the compound of Example 12, and thus the compound of Example 11 shows higher inhibitory activity to human GGT as compared with the compound of Example 12.

It is supposedly attributed to that the compounds of Examples 8, 10, 11 and 16 have structures close to the substrate structure of human GGT and therefore fitted in the substrate recognition site in the active center of human GGT to cause close interaction and quickly inactivate human GGT.

As described, since the inhibitory activity of the compounds to E. coli GGT depends on the chemical reactivity and the inhibitory activity of the compounds to human GGT depends not only on chemical reactivity but also on the compatibility with the substrate recognition site of the enzyme, it is possible to obtain a stable inhibitor selectively reactive on human GGT by designing the molecules in a manner that the chemical reactivity is suppressed as much as possible and the structure compatible with the substrate recognition site of human GGT is incorporated therein. On the contrary, it is possible to obtain an inhibitor having high inhibitory activity to E-coli GGT by increasing the chemical reactivity and making the structure that is compatible with the substrate recognition part of human GGT not to be incorporated therein.

[Inhibitory Activity of Compound of Example 8 to GGT]

From the enzyme activity curves shown in the above FIG. 1 (fluorescence intensity of AMC released from substrate in the case reaction of the compound of Example 8 as one example of inhibitors and E-coli GGT) and the above FIG. 2 (fluorescence intensity of AMC in the case reaction of the compound of Example 8 as one example of inhibitors and human GGT), it can be understood that the compound of Example 8 causes special inhibition for both E-coli GGT and human GGT being gradually inactivated with the lapse of time.

That is, in common inhibitors, as the amount of the inhibitor is increased, the slope of an activity plots becomes smaller, however the activity plots are not curves but linear. In this case, if the inhibitor is removed by any method from a mixture of GGT and the inhibitor, GGT regain the activity as it has before.

On the other hand, the activity plot of the compound of Example 8 has a slope becoming smaller with the lapse of time. It is because GGT is inactivated with the lapse of time by the compound of Example 8 and the activity becomes finally zero. In this case, if GGT is once inactivated, even if the inhibitor is removed, the activity of GGT is not restored. Therefore, the compound of Example 8 is an inhibitor that can irreversibly inactivate GGT. As compared with general inhibitors for reversibly inhibiting GGT, it has a high inhibitory effect on GGT.

[Chemical Stability]

The hydrolysis ratios of the compounds of Examples 1 to 11 are shown in Table 3. Herein, the hydrolysis ratios of the reactive compounds of Examples 1 to 11 were measured after the respective compounds were stored in water at room temperature. In this connection, the compounds other than the compound of Example 10 were stored in water for 12 hours and the compound of Example 10 was stored in water for 112 hours.

TABLE 3

|  | Hydrolysis ratio (%) |
| --- | --- |
| Example 1 | 0 |
| Example 2 | 0 |
| Example 3 | 0 |
| Example 4 | 0 |
| Example 5 | 0 |
| Example 6 | 12.3 |
| Example 7 | 48.6 |
| Example 8 | 6.0 |
| Example 9 | 0 |
| Example 10 | 37.5* |
| Example 11 | 0 |

From the results shown in Table 3, it can be understood that the hydrolysis ratios of the compounds of Examples 1 to 5, 9, and 11 are zero, that is, these compounds are not hydrolyzed and chemically stable. Particularly, the compound of Example 11 has, as shown in Table 2, inhibitory activity to human GGT as high as those of Examples 6 and 10 and also, as shown in Table 3, lower hydrolysis ratio than those of Examples 6 and 10. Accordingly, the compound of Example 11 can stably cause high inhibitory effect on human GGT.

Further, the hydrolysis ratio of the compound of Example 7 in alkaline, neutral, or acidic condition is shown in Table 4. Herein, the compound of Example 7 was dissolved in a solvent shown in Table 4 and kept at 23.5° C., and the hydrolysis ratio of the compound of Example 7 was measured after 12 hours.

TABLE 4

| Solvent | pH | Hydrolysis ratio (%) |
| --- | --- | --- |
| 0.1 N Na$_2$CO$_3$ | 11.6 | 100 |
| 0.1 N NaHCO$_3$ | 8.3 | 100 |
| D$_2$O | 7 | 49 |
| 0.1 N CH$_3$COOD | 2.9 | 40 |
| 0.1 N CF$_3$COOD | <1 | 0 |
| 0.1 N DCl | <1 | 0 |
| 0.1 N DCl + MeOH | <1 | 0 |

From the results shown in Table 4, the compound of Example 7 was hydrolyzed under alkaline and neutral conditions, and particularly, the hydrolysis ratio of the compound of Example 7 was high under the alkaline condition. However, under the acidic condition, the hydrolysis ratio of the compound of Example 7 was low and the compound of Example 7 is little hydrolyzed and thus stable. Therefore, it is supposed that under the acidic condition, the compound of Example 7 can be stored stably and cause a stable inhibitory effect on GGT.

The compound of Example 7 has, as shown in Table 3, the highest hydrolysis ratio among the compounds of Examples 1 to 11 and is thus the most easily hydrolysable and unstable compound. Accordingly, since the compound of Example 7 is stable in acidic condition, the other compounds of Examples 1 to 6 and 8 to 11 are supposed to be stable at least in acidic condition.

According to experiments carried out by the inventors of this invention or the like, it was confirmed that even if 10 mM of the compound of Example 11 was added to a glutamine-dependent asparagine synthetase, a typical glutamine amide transferase, and incubated for 2 hours, the compound of Example 11 did not inhibit the function of the glutamine-dependent asparagine synthetase, at all. Therefore, the phosphonic acid diester derivative (1) specifically reacts on GGT.

Although the present invention has been described and illustrated in detail, it is clearly understood that the same is by way of illustration and example only and is not to be taken by way of limitation, the spirit and scope of the present invention being limited only by the terms of the appended claims.

What is claimed is:

1. A phosphonic acid diester derivative represented by formula (1):

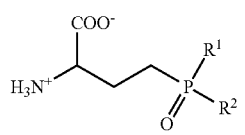

(1)

wherein $R^1$ is $OR^{10}$; and
$R^2$ is $OR^{11}$;
wherein $R^{10}$ is an optionally substituted alkyl group or an optionally substituted aryl group; and
$R^{11}$ is an optionally substituted aryl group.

2. The phosphonic acid diester derivative according to claim 1, wherein substituent groups of said optionally substituted alkyl group include at least one group selected from the group consisting of an optionally substituted phenyl group, a nitrogen-containing heterocyclic group, an alkylsulfanyl group, an arylsulfanyl group, a hydroxy group, a carbamoyl group, an amino group, a guanidino group, an alkoxy group, an amido group, a carboxy group, and an equivalent group of a carboxy group.

3. The phosphonic acid diester derivative according to claim 1, wherein $R^{10}$ is an optionally substituted alkyl group represented by formula (7);

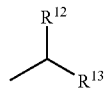

(7)

wherein $R^{12}$ is an optionally substituted alkyl group, an optionally substituted aryl group, or a hydrogen atom and $R^{13}$ is a hydrogen atom or a group represented by the following general formula (8);

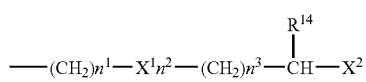

(8)

wherein $n^1$ is an integer between 0 and 4;
$n^2$ is an integer between 0 or 1;
$n^3$ is an integer between 0 and 4;
$X^1$ is an amido group or an alkenyl group;
$X^2$ is a carboxy group or an equivalent group of a carboxy group;
and $R^{14}$ is a hydrogen atom or a lower alkyl group.

4. The phosphonic acid diester derivatives according to claim 3, wherein $X^2$ is selected from the group consisting of —COOR, —CONR$_2$, —COR, —CN, —NO$_2$ —NHCOR, —OR, —SR, —OCOR, —SO$_3$R, and —SO$_2$NR$_2$;
wherein R is a hydrogen atom or an alkyl group.

5. The phosphonic acid diester derivative according to claim 3, wherein $R^{12}$ is an optionally substituted alkyl group selected from the group consisting of an optionally substituted phenyl group, a nitrogen-containing heterocyclic group, an alkylsulfanyl group, an acrylsulfanyl group, a hydroxy group, a carbamoyl group, an amino group, a guanidino group, an alkoxy group, and an amido group.

6. The phosphonic acid diester derivative according to claim 1, wherein $R^{10}$ is an optionally substituted aryl group wherein at least one substituent group is selected from the group consisting of an alkyl group that may be substituted with a carboxy group or an equivalent group of a carboxy group, an electron-withdrawing group, a carboxy group, and an equivalent group of a carboxy group.

7. The phosphonic acid diester derivative according to claim 1, wherein $R^{10}$ is said optionally substituted aryl group with at least one substituent group being an optionally substituted phenyl group.

8. The phosphonic acid diester derivative according to claim 7, wherein said optionally substituted phenyl group is represented by formula (9):

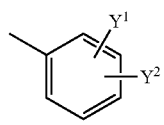

(9)

wherein $Y^1$ is selected from the group consisting of —R', —OR', and an electron-withdrawing group;
$Y^2$ is a group selected from the group consisting of an alkyl group that may be substituted with a carboxy group or an equivalent group of a carboxy group and may have a double bond, a hydrogen atom, a carboxy group, and an equivalent group of a carboxy group;
wherein $Y^1$ and $Y^2$ may be bonded to each other to form a ring;
and R' is a hydrogen atom or an alkyl group that may have a double bond.

9. The phosphonic acid diester derivatives according to claim 6, wherein the electron-withdrawing group is at least one group selected from the group consisting of a halogen atom, —COOR', —CONR'$_2$, —COR', —OCOR', —CF$_3$, —CN, —SR', —S(O)R', —SO$_2$R', —SO$_2$NR'$_2$, —PO(OR')$_2$, and —NO$_2$;
and R' is a hydrogen atom or an alkyl group that may have a double bond.

10. The phosphonic acid diesters derivative according to claim 6, wherein the carboxy group and the equivalent group of a carboxy group independently are at least one group selected from the group consisting of —COOR", —CONR"$_2$, —COR", —CN, —NO$_2$, —NHCOR", —OR", —SR", —OCOR", —SO$_3$R", and —SO$_2$NR"$_2$;
and R" denotes a hydrogen atom or an alkyl group that may have a double bond.

11. A phosphonic acid diester derivative represented by formula (10):

(10)

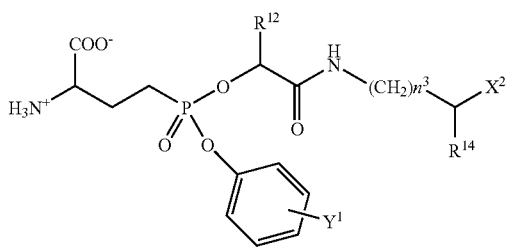

wherein $R^{12}$ is an optionally substituted alkyl group, an optionally substituted aryl group, or a hydrogen atom;

$n^3$ n is an integer between 0 and 4;

$X^2$ is a carboxy group or an equivalent group of a carboxy group;

$Y^1$ is selected from the group consisting of —R', —OR', and an electron-withdrawing group;

R' is a hydrogen atom or an alkyl group that may have a double bond;

and $R^{14}$ is a hydrogen atom or a lower alkyl group.

12. A phosphonic acid diester derivative represented by formula (11):

(11)

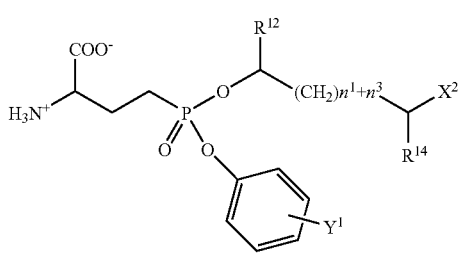

wherein $R^{12}$ is an optionally substituted alkyl group, an optionally substituted aryl group, or a hydrogen atom $n^1$ is an integer between 0 and 4;

$n^3$ is an integer between 0 and 4;

$X^2$ is a carboxy group or an equivalent group of a carboxy group;

$Y^1$ is selected from the group consisting of —R', —OR', and an electron-withdrawing group;

R' is a hydrogen atom or an alkyl group that may have a double bond;

and $R^{14}$ is a hydrogen atom or a lower alkyl group.

13. A phosphonic acid diester derivative represented by formula (12):

(12)

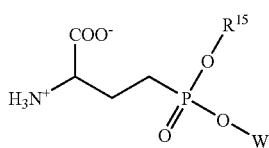

wherein $R^{15}$ is a lower alkyl group; and

W is a group represented by formulas (13) to (16);

(13)

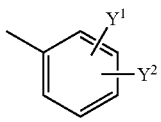

(14)

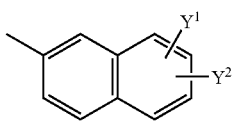

(15)

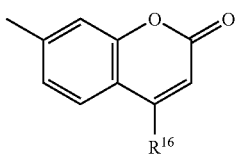

(16)

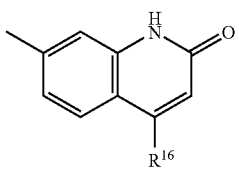

wherein $R^{16}$ is a hydrogen atom or a lower alkyl group, $Y^1$ is selected from the group consisting of —R', —OR', and an electron-withdrawing group;

$Y^2$ is a group selected from the group consisting of an alkyl group that may be substituted with a carboxy group or an equivalent group of a carboxy group and may have a double bond, a hydrogen atom, a carboxy group, and an equivalent group of a carboxy group; and R' is a hydrogen atom or an alkyl group that may have a double bond.

14. A phosphonic acid diester derivative represented by formula (17):

(17)

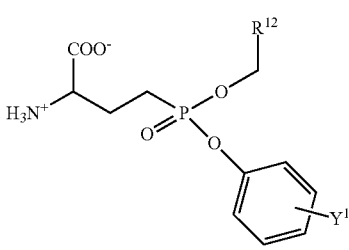

Wherein $Y^1$ is selected from the group consisting of —R', —OR', and an electron-withdrawing group;

R' is a hydrogen atom or an alkyl group that may have a double bond;

and $R'^{12}$ is an optionally substituted alkyl group, an optionally substituted aryl group, or a hydrogen atom.

15. A phosphonic acid diester derivative represented by formula (18):

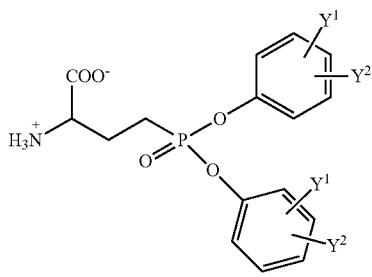

(18)

Wherein $Y^1$ is selected from the group consisting of —R', —OR', and an electron-withdrawing group;

$Y^2$ is a group selected from the group consisting of an alkyl group that may be substituted with a carboxy group or an equivalent group of a carboxy group and may have a double bond, a hydrogen atom, a carboxy group, and an equivalent group of a carboxy group; and R' is a hydrogen atom or an alkyl group that may have a double bond.

16. A 2-substituted amino-4-phosphonobutanoic acid metal salt represented by formula (19):

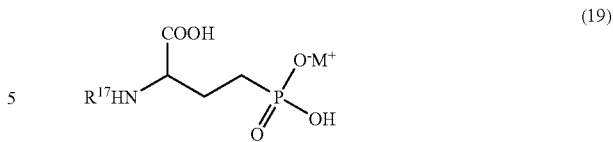

(19)

wherein M is an alkali metal and $R^{17}$ is an alkoxycarbonyl group containing an optionally substituted aromatic hydrocarbon group.

17. A 2-substituted amino-4-phosphonobutanoic acid ester represented by formula (20):

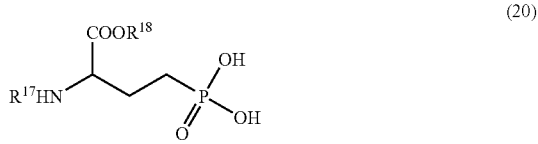

(20)

wherein $R^{18}$ is an optionally substituted aromatic hydrocarbon group and $R^{17}$ is an alkoxycarbonyl group containing an optionally substituted aromatic hydrocarbon group.

* * * * *